(12) United States Patent
Kubach et al.

(10) Patent No.: US 11,000,187 B2
(45) Date of Patent: May 11, 2021

(54) SYSTEMS AND METHODS FOR IMPROVED MONTAGING OF OPHTHALMIC IMAGING DATA

(71) Applicant: Carl Zeiss Meditec, Inc., Dublin, CA (US)

(72) Inventors: Sophie Kubach, Menlo Park, CA (US); Ali Fard, Dublin, CA (US); Jennifer Y. Luu, Walnut Creek, CA (US); Mary K. Durbin, San Francisco, CA (US); Matthew J. Everett, Livermore, CA (US); Conor Leahy, Dublin, CA (US); Luis De Sisternes, San Francisco, CA (US); Kevin Meng, Mountain View, CA (US); Gregory G. Anderson, Hayward, CA (US); Katherine Makedonsky, Berkeley, CA (US)

(73) Assignee: CARL ZEISS MEDITEC, INC., Dublin, CA (US)

( * ) Notice: Subject to any disclaimer, the term of this patent is extended or adjusted under 35 U.S.C. 154(b) by 434 days.

(21) Appl. No.: 16/123,079

(22) Filed: Sep. 6, 2018

(65) Prior Publication Data
US 2019/0069775 A1   Mar. 7, 2019

Related U.S. Application Data

(60) Provisional application No. 62/555,442, filed on Sep. 7, 2017.

(51) Int. Cl.
*A61B 3/10* (2006.01)
*A61B 3/12* (2006.01)
(Continued)

(52) U.S. Cl.
CPC ........... *A61B 3/102* (2013.01); *A61B 3/0058* (2013.01); *A61B 3/12* (2013.01); *A61B 3/1225* (2013.01);
(Continued)

(58) Field of Classification Search
CPC ..................................................... A61B 3/102
(Continued)

(56) References Cited

U.S. PATENT DOCUMENTS

| 4,170,398 A | 10/1979 | Koester |
| 4,732,466 A | 3/1988 | Humphrey |

(Continued)

FOREIGN PATENT DOCUMENTS

| EP | 2702931 A2 | 3/2014 |
| WO | 1999/005988 A2 | 2/1999 |

(Continued)

OTHER PUBLICATIONS

Blazkiewicz et al., "Signal-To-Noise Ratio Study of Full-Field Fourier-Domain Optical Coherence Tomography", Applied Optics, vol. 44, No. 36, Dec. 20, 2005, pp. 7722-7729.

(Continued)

*Primary Examiner* — James C. Jones
(74) *Attorney, Agent, or Firm* — Morrison & Foerster LLP

(57) ABSTRACT

An ophthalmic imaging system provides a user interface to facilitate the montaging of scan images collected with various imaging modalities, such as images collected with a fundus imaging system or an optical coherence tomography (OCT) system. The amount of each constituent image used in the montage is dependent upon its respective quality. During the collecting of scans (constituent images) for montaging, any scan may be designated for rescanning, such as if its current quality is deemed less than sufficient. In the (Continued)

case of using an OCT system to collect constituent images (e.g., cube scans), the scanned region of a constituent image may be modified based on physical characteristics of the eye being scanned.

24 Claims, 18 Drawing Sheets
(4 of 18 Drawing Sheet(s) Filed in Color)

(51) Int. Cl.
| | |
|---|---|
| A61B 3/00 | (2006.01) |
| G06T 5/50 | (2006.01) |
| G06T 7/33 | (2017.01) |
| G06T 3/40 | (2006.01) |
| A61B 3/15 | (2006.01) |
| G06T 7/00 | (2017.01) |

(52) U.S. Cl.
CPC .............. *G06T 3/4038* (2013.01); *G06T 5/50* (2013.01); *G06T 7/337* (2017.01); *A61B 3/152* (2013.01); *G06T 7/0012* (2013.01); *G06T 2200/24* (2013.01); *G06T 2200/32* (2013.01); *G06T 2207/10016* (2013.01); *G06T 2207/30041* (2013.01); *G06T 2207/30168* (2013.01)

(58) Field of Classification Search
USPC ......................................................... 351/206
See application file for complete search history.

(56) References Cited

U.S. PATENT DOCUMENTS

| | | | |
|---|---|---|---|
| 6,322,216 | B1 | 11/2001 | Yee et al. |
| 7,301,644 | B2 | 11/2007 | Knighton et al. |
| 8,223,143 | B2 | 7/2012 | Dastmalchi et al. |
| 8,224,050 | B2 | 7/2012 | Doering et al. |
| 8,332,016 | B2 | 12/2012 | Stetson |
| 9,778,021 | B2 | 10/2017 | Bagherinia |
| 2007/0076958 | A1 | 4/2007 | Venkatesh |
| 2010/0094262 | A1 | 4/2010 | Tripathi et al. |
| 2013/0176532 | A1 | 7/2013 | Sharma et al. |
| 2014/0232987 | A1 | 8/2014 | Westphal et al. |
| 2014/0320810 | A1 | 10/2014 | Fukuma et al. |
| 2015/0131050 | A1 | 5/2015 | Bublitz et al. |
| 2016/0066778 | A1* | 3/2016 | Imamura .............. A61B 3/1241 351/206 |
| 2016/0227999 | A1 | 8/2016 | An et al. |
| 2017/0032564 | A1 | 2/2017 | Dastmalchi et al. |
| 2017/0316565 | A1 | 11/2017 | Leahy et al. |

FOREIGN PATENT DOCUMENTS

| | | |
|---|---|---|
| WO | 2012/059236 A1 | 5/2012 |
| WO | 2015/189174 A2 | 12/2015 |
| WO | 2016/124644 A1 | 8/2016 |
| WO | 2017/218738 A1 | 12/2017 |
| WO | 2018/178269 A1 | 10/2018 |
| WO | 2019/030375 A2 | 2/2019 |

OTHER PUBLICATIONS

Bonin et al., "In Vivo Fourier-Domain Full-Field OCT of the Human Retina with 1.5 Million A-lines/s", Optics Letters, vol. 35, No. 20, Oct. 15, 2010, pp. 3432-3434.
Brown et al., "Automatic Panoramic Image Stitching using Invariant Features", International Journal of Computer Vision, vol. 74, No. 1, 2007, pp. 59-73.
Brown et al., "Recognising Panoramas", In Proceedings of the 9th International Conference on Computer Vision, vol. 2, Oct. 2003, 8 pages.
Fercher et al., "Eye-Length Measurement by Interferometry with Partially Coherent Light", Optics Letters, vol. 13, No. 3, Mar. 1988, pp. 186-188.
Grajciar et al., "Parallel Fourier Domain Optical Coherence Tomography for in Vivo Measurement of the Human Eye", Optics Express, vol. 13, No. 4, Feb. 21, 2005, pp. 1131-1137.
Hiratsuka et al., "Simultaneous Measurements of Three-Dimensional Reflectivity Distributions in Scattering Media based on Optical Frequency-Domain Reflectomety", Optics Letters, vol. 23, No. 18, Sep. 15, 1998, pp. 1420-1422.
Huang et al., "Optical Coherence Tomography", Science, vol. 254, No. 5035, Nov. 22, 1991, pp. 1178-1181.
Invitation to Pay Addition Fees received for PCT Patent Application No. PCT/EP2018/071744, dated Dec. 6, 2018, 11 pages.
Klein et al., "Joint Aperture Detection for Speckle Reduction and Increased Collection Efficiency in Ophthalmic MHz OCT", Biomedical Optics Express, vol. 4, No. 4, Apr. 1, 2013, pp. 619-634.
Kwatra et al., "Graphcut Textures: Image and Video Synthesis Using Graph Cuts", In ACM Transactions on Graphics (ToG), vol. 22, No. 3, Available at <http://www.cc.gatech.edu/cpl/projects/graphcuttextures>, 2003, 10 pages.
Lee et al., "Line-Field Optical Coherence Tomography Using Frequency-Sweeping Source", IEEE Journal of Selected Topics in Quantum Electronics, vol. 14, No. 1, Jan./Feb. 2008, pp. 50-55.
Li et al., "Automatic Montage of SD-OCT Data Sets", Optics Express, vol. 19, No. 27, Dec. 19, 2011, pp. 26239-26248.
Mujat et al., "Swept-Source Parallel OCT", Proc. of SPIE, vol. 7168, 2009, pp. 71681E-1-71681E-8.
MySQL, "21.6.10 NDB Cluster Replication: Multi-Master and Circular Replication", MySQL 5.7 Reference Manual, Available Online at <https://dev.mysql.com/doc/refman/5.7/en/mysql-cluster-replication-multi-master.html>, Sep. 1, 2017, pp. 1-8.
Nakamura et al., "High-Speed Three-Dimensional Human Retinal Imaging by Line-Field Spectral Domain Optical Coherence Tomography", Optics Express, vol. 15, No. 12, Jun. 11, 2007, pp. 7103-7116.
Nankivil et al., "Coherence Revival Multiplexed, Buffered Swept Source Optical Coherence Tomography: 400 kHz Imaging with a 100 kHz Source", Optics Letters, vol. 39, No. 13, Jul. 1, 2014, pp. 3740-3743.
Potsaid et al., "Ultrahigh Speed 1050nm Swept Source / Fourier Domain OCT Retinal and Anterior Segment Imaging at 100,000 to 400,000 Axial Scans per Second", Optics Express, vol. 18, No. 19, Sep. 13, 2010, pp. 20029-20048.
Považay et al., "Full-Field Time-Encoded Frequency-Domain Optical Coherence Tomography", Optics Express, vol. 14, No. 17, Aug. 21, 2006, pp. 7661-7669.
"Seam Estimation", Available at <https://docs.opencv.org/2.4/modules/stitching/doc/seam_estimation.html#detail-voronoiseamfinder>, Aug. 11, 2017, pp. 1-4.
Shi et al., "Good Features to Track", IEEE Conference on Computer Vision and Pattern Recognition (CVPR94), Jun. 1994, 8 pages.
Thévenaz et al., "User-Friendly Semiautomated Assembly of Accurate Image Mosaics in Microscopy", Microscopy Research and Technique, vol. 70, 2007, pp. 135-146.
Wieser et al., "Multi-Megahertz OCT: High Quality 3D imaging at 20 Million A-scans and 4.5 GVoxels Per Second", Optics Express, vol. 18, No. 14, Jul. 5, 2010, pp. 14685-14704.
Zhang et al., "Minimizing Projection Artifacts for Accurate Presentation of Choroidal Neovascularization in OCT Micro-Angiography", Biomedical Optics Express, vol. 6, No. 10, Oct. 1, 2015, pp. 4130-4143.
Zhang et al., "Projection-Resolved Optical Coherence Tomographic Angiography", Biomedical Optics Express, vol. 7, No. 3, Mar. 1, 2016, pp. 816-828.
Zuluaga et al., "Spatially Resolved Spectral Interferometry for Determination of Subsurface Structure", Optics Letters, vol. 24, No. 8, Apr. 15, 1999, pp. 519-521.

* cited by examiner

SYSTEMS AND METHODS FOR IMPROVED MONTAGING OF OPHTHALMIC IMAGING DATA

PRIORITY

This application claims priority to U.S. Provisional Application Ser. No. 62/555,442 filed Sep. 7, 2017, the contents of which are hereby incorporated by reference.

FIELD OF INVENTION

The present invention is generally directed to the field of ophthalmic imaging systems. More specifically, it is directed to techniques for montaging two or more scans obtained with the ophthalmic imaging system.

BACKGROUND

A wide variety of interferometric based imaging techniques have been developed to provide high resolution structural information of samples in a range of applications. Optical Coherence Tomography (OCT) is an interferometric technique that can provide images of samples including tissue structure on the micron scale in situ and in real time (Huang, D. et al., Science 254, 1178-81, 1991). OCT is based on the principle of low coherence interferometry (LCI) and determines the scattering profile of a sample along the OCT beam by detecting the interference of light reflected from a sample and a reference beam (Fercher, A. F. et al., Opt. Lett. 13, 186, 1988). Each scattering profile in the depth direction (z) is reconstructed individually into an axial scan, or A-scan. Cross-sectional images (B-scans), and by extension 3D volumes, are built up from many A-scans, with the OCT beam moved to a set of transverse (x and y) locations on the sample.

Optical coherence tomography (OCT) is a noninvasive, noncontact imaging modality that uses coherence gating to obtain high-resolution cross-sectional images of tissue microstructure. Several implementations of OCT have been developed. In time domain OCT (TD-OCT), the path length between light returning from the sample and reference light is translated longitudinally in time to recover the depth information in the sample. In Frequency domain OCT (FD-OCT), the interferometric signal between light from a reference and the back-scattered light from a sample point is recorded in the frequency domain either by using a dispersive spectrometer in the detection arm in the case of spectral-domain OCT (SD-OCT) or rapidly tuning a swept laser source in the case of swept-source OCT (SS-OCT). After a wavelength calibration, a one-dimensional Fourier transform is taken to obtain an A-line spatial distribution of the object scattering potential, e.g. an A-scan.

Functional OCT can provide important clinical information that is not available in typical OCT images, which are intensity based and provide structural information. There have been several functional contrast enhancement methods including Doppler OCT, Phase-sensitive OCT measurements, Polarization Sensitive OCT, Spectroscopic OCT, etc. Integration of functional extensions can greatly enhance the capabilities of OCT for a range of applications in medicine.

One of the most promising functional extensions of OCT has been the field of OCT angiography which is based on flow contrast. Visualization of the detailed vasculature using OCT could enable doctors to obtain new and useful clinical information for diagnosis and management of eye diseases in a non-invasive manner. Fluorescein angiography and indocyanine green (ICG) angiography are currently the gold standards for vasculature visualization in the eye. However, the invasiveness of these approaches combined with possible complications (allergy to dyes and side effects) make them unsuitable techniques for widespread screening applications in ophthalmic clinics. There are several flow contrast techniques in OCT imaging that utilize the change in data between successive B-scans or frames (inter-frame change analysis) of the OCT intensity or phase-resolved OCT data. A B-scan is a collection of adjacent A-scan (typically arranged linearly) defining a two-dimensional (2D) image along an axial direction of a scan beam. One of the major applications of such techniques has been to generate en face vasculature images of the retina. An en face image, or face image projection is a 2D frontal view of segmented tissue layer. For example, in the case of structural OCT, an en face image may typically be generated by projecting the average reflectance signal intensity over depth onto a 2D canvas, which may be parallel to a plane of the retina. High resolution en face visualization based on inter-frame change analysis requires high density of sampling points and hence the time required to finish such scans can be up to an order of magnitude higher compared to regular cube scans used in commercial OCT systems. A cube scan (or data cube or volume) is a collection of adjacent B-scans that define a three-dimensional (3D) scan of a volume.

The large acquisition times and huge data volumes make it challenging to obtain high resolution data over large fields of view (FOV). Acquisition of multiple smaller data cubes of smaller FOV and montaging them together to generate images and analysis over larger FOV has been described (see for example, Y. Li et al., "Automatic montage of SD-OCT data sets," Optics Express, 19, 26239-26248 (2011) and US Pat. App. Pub. 2013/0176532, the contents of which are hereby incorporated by reference).

Montaging is also used to expand the field of view in fundus imaging systems. Montaging of fundus images can aid clinicians by providing a more complete view of the retina. Fundus image montaging is a common technique for extending the imaged field-of-view, and has been offered as a feature on fundus cameras, including the Zeiss VISU-CAM® and Heidelberg SPECTRALIS®. Applicants have described different aspects of montaging related to OCT and fundus imaging in the past (see for example US Pat. App. Pub. No. 20170316565, International Pat. App. PCT/EP2018/071744, US Pat. App. Pub. 2013/0176532, and US Pat. App. Pub. No. 2016/0227999, the contents of which are hereby incorporated by reference).

It is an object of the present invention to provide improvements and enhancements to systems and methods for montaging image data of the eye of a patient.

It is a further object of the present invention to provide a method/system for optimizing/customizing scan patterns to the physical characteristics of a patient's eye.

SUMMARY

The above objects are met in a system and method for improved montaging of retinal images. In one embodiment, a particular acquisition work flow is presented that reduces the total time the patient must remain still in front of an imaging instrument. In another embodiment, an ophthalmic imaging system offers the user different montaging modes where the amount of overlap between the constituent images in the montage can be varied depending upon the curvature of the eye. In yet another embodiment, montage configurations comprising images of different sizes and resolutions are described. In one or more embodiments, a preliminary scan (or "prescan") can be used to identify the optimal overlap between constituent images to be montaged and to optimize the scan sizes (e.g., dimension of scanned areas) and scan locations for a particular eye. In a further embodiment, a system or method is described for applying artifact removal to all the constituent images in a montage. In another embodiment, the system or method performs a quality check on the montaged image to confirm that the acquired, constituent images are placed in their correct relative location within the final montage.

In embodiments, a method/system/device is provided for collecting a set of images for montaging. The set of images may be collected using an ophthalmic imaging system, such as an OCT system or a fundus imager. A user interface provides a scan option that includes two or more scans covering different transverse regions on the retina of a patient, with some overlap between pairs of regions. Upon selection of the scan option, capture of the two or more scans for the selected scan option is initiated. The collected two or more scans are displayed for approval. The collected two or more scans can be displayed separately or as a montaged image. In response to user selection of any of the displayed scans by use of a user input device, the selected scans are automatically retaken and the display is updated with the recaptured scans. If the two or more scans are displayed separately for approval (e.g., not montaged), then the displayed scans may be montaged after a user input indicating user approval.

Alternatively, if the two or more scans are displayed as a montaged image, the user selection may be applied to at least one constituent scan within the montaged image. Additionally, the two or more scans may have preassigned displacement positions relative to each other within the montaged image. In this case, a processor may process the montaged image to determine if the two or more scans are in their preassigned displacement positions relative to each other in the montaged image, and identify any misplaced scan or display an error indicator based on the determination. Optionally, a scan displacement input may be provided in the user interface, wherein the preassigned displacement positions relative to each other of the two or more scans may be adjusted by use of the scan displacement input. Additionally, in response to failing to capture any of the two or more scans for the selected scan option, the failed scans may be excluded from the montaged image. In place of a failed scan, a failure indicator may be displayed within the montaged image at a location corresponding to where failed scans would have been if it had not failed. A user may select the failure indicator, which may cause an automatic recapturing of the scan corresponding to the selected failure indictors and an updating of the montaged image with the recaptured scan. Optionally, the failure indicators may include any of a textual description of failure, a graphic representation of failure, and/or a highlighted border indicating an outline of the failed scan within the montaged image.

Optionally, any of the collected scans may be retaken prior to montaging based on an approval input from the user. That is, montaging may not necessarily be initiated immediately after collecting the scans associated with the selected scan option. Rather, the system or an operator is given an opportunity to review the individual scans to determine if they are of sufficient (e.g., minimum) quality prior to montaging. For example, the system may determine a numerical quality factor (or measure) for each scan (e.g., ranging from 1 to 10, with 10 indicating top quality), and any scan whose determined quality factor is not higher than a predefined, minimum quality factor (e.g., 6), may be rescanned until a scan meeting the minimum quality factor is achieved. Similarly, the operator may visually inspect the displayed scans and determine if they are of sufficient quality for montaging. The operator may select (e.g., designate by use of a user input) any collected scan for rescanning. Irrespective, after satisfactory scans are collected, the constituent scans (e.g., images) may be montaged, and the montaged image may be stored, displayed, or submitted to further analysis.

In embodiments, the two or more scans of the scan option may cover differently sized regions of the retina. That is, each scan may span a differently sized area of the retina, such as one scan spanning a 3×3 mm area and another spanning a 6×6 mm area. Additionally, each scan may be of different resolution. For example, if the fundus imaging system is an OCT system and each scan region has an equal number of B-scans, then changing the size of a scan region will change the resolution of that scan region.

Furthermore, the montaged image may be comprised of different fractions of each of the two or more scans of the scan option. That is the system may identify the higher quality images in a scan option, and use larger amounts of the higher quality scans to construct the montaged image. For example, if the system assigns a quality factor, or other quality measure, to each of the captured two or more scans, then the captured scans having higher quality factors may comprise larger fractions of the montaged image, and scans having lower quality measures may make up smaller portions of the montaged image.

The system may incorporate additional quality checks. For example, the two or more scans of the scan option may have preassigned displacement positions/locations relative to each other, and the montaged image may be checked to ensure that each scan is at its preassigned position. Any misplaced scan may be identified and/or an error may be issued. For instance, if the scan option is comprised of two scans, then the system may assign the first scan to a left-most position in the montaged image, and the second scan to a right-most position in the montaged image. The location of each scan within the eye may be controlled by use of fixation light. In another example where the scan option is comprised of five scans, one scan may be preassigned a center location within the montaged image, and the remaining four scans may be preassigned (e.g., by scan sequence) to specific quadrants along the periphery of the center scan.

Optionally, the user interface may include a user input for removing artifacts, such as image artifacts from individual scans and/or from the montaged image.

The present invention is also embodied in a method/system/device for generating a montaged fundus image of an eye. The montaged image may be generated using an ophthalmic imaging system, which may be an OCT system or a fundus imager. A user interface provides multiple scan options, where each scan option includes (e.g., defines) two or more scans covering different transverse regions on the retina of a patient with some overlap portion between scans. Each of the different scan options, however, may define a different amount of overlap among its respective two or more scans. For example, one scan option may define more tightly overlapping scans than another. Upon selection of a scan option from among the multiple scan options, capture of the two or more scans included the selected scan option (e.g., defined by the selected scan option) is initiated. The captured two or more scans may then be combined into a single montaged image, which may be stored, displayed or submitted for further analysis.

Optionally, the user interface further may provide a separate scan status for each of two or more scans during the capture of the two or more scans. For example, if the two or more scans are collected in sequence, the user interface may provide an indicator specifying what portion of the retina is current being scanned (e.g. indicate which of the two or more scan is currently being collected, and/or which scan has already been collected). The user interface may also provide a user input for recapturing a selected one or more of the two or more scans during the capture of the two or more scans. For example, if the operator notes a situation that may affect the scan (e.g., an eye blink or patient movement), the operator may indicate that a current scan (among the two or more scans) should be rescanned.

Each of the plurality of scan options may be separately optimized for a different eye curvature. For example, eyes with higher curvature may benefit from a scan option that provides a larger overlap among its two or more scans. Optionally, a prescan of the eye (e.g., prior to collecting the two or more scans of a scan option) may be collected to determine an optimal scan pattern for use during the capture of the two or more scans based on the curvature of the eye. That is, the prescan may be used to determine an optimal scan pattern. For example, the prescan may determine if a designated scan would be ill-affected by the curvature of the eye prior to the designated scan being collected. In some embodiments, one of the multiple of scan options may be selected, or recommended, based on the determined optimal scan pattern. The prescan may be of lower resolution than the capture of the two or more designated scans.

An example of the use of this prescan would be if the ophthalmic imaging system were an optical coherence tomographic (OCT) system, and the two or more scans of one of the multiple scan options included a central scan and a periphery scan that is peripheral to the central scan. In this case, prior to the capture of the central scan and/or the periphery scan, a survey B-scan may be applied as a prescan within a region corresponding to where the periphery scan is to be captured. If a portion of the survey B-scan is not fully resolved within the imaging depth capability of the OCT system, then the designated scan region of the periphery scan may be shifted (or offset) to increase its overlap with the central scan and thus move it to less curved region of the retina. Conversely, if the survey B-scan is fully resolved within the imaging depth capability of the OCT system, then the designated scan region of the periphery scan may be shifted to decrease its overlap with the central scan, which increases the total area covered by the two scans. This would provide for a larger field of view for the final montaged image. In this way the scan pattern of each scan option may be further adjusted dependent upon the curvature of the patient's eye (e.g., as determined by the prescan).

Various embodiments may also include additional error detection. For example, the two or more scans of an individual scan option may be designated preassigned positions relative to each other. In this case, the montaged image may be processed to determine if its two or more constituent scans are in their respective, preassigned positions relative to each other. Any misplaced scan may be identified, or an error message may be issued based on the determination.

To further improve the montaging of the two or more scans of a scan option, the amount contributed by each constituent scan to the final montaged image may be made dependent upon the quality of each constituent scan. For example, a quality measure may be determined for each of the captured two or more scans prior to montaging, and captured scans having higher quality measures may be selected to make up larger portions of the final montaged image.

Other objects and attainments together with a fuller understanding of the invention will become apparent and appreciated by referring to the following description and claims taken in conjunction with the accompanying drawings.

The embodiments disclosed herein are only examples, and the scope of this disclosure is not limited to them. Embodiments according to the invention are disclosed in the attached claims directed to a method, a storage medium, a system, a device and/or a computer program product, wherein any feature mentioned in one claim category, e.g. method, can be claimed in another claim category, e.g. system, as well. The dependencies or references back in the attached claims are chosen for formal reasons only. However, any subject matter resulting from a deliberate reference back to any previous claims can be claimed as well, so that any combination of claims and the features thereof are disclosed and can be claimed regardless of the dependencies chosen in the attached claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In the drawings wherein like reference symbols/characters refer to like parts.

Figure 4A:
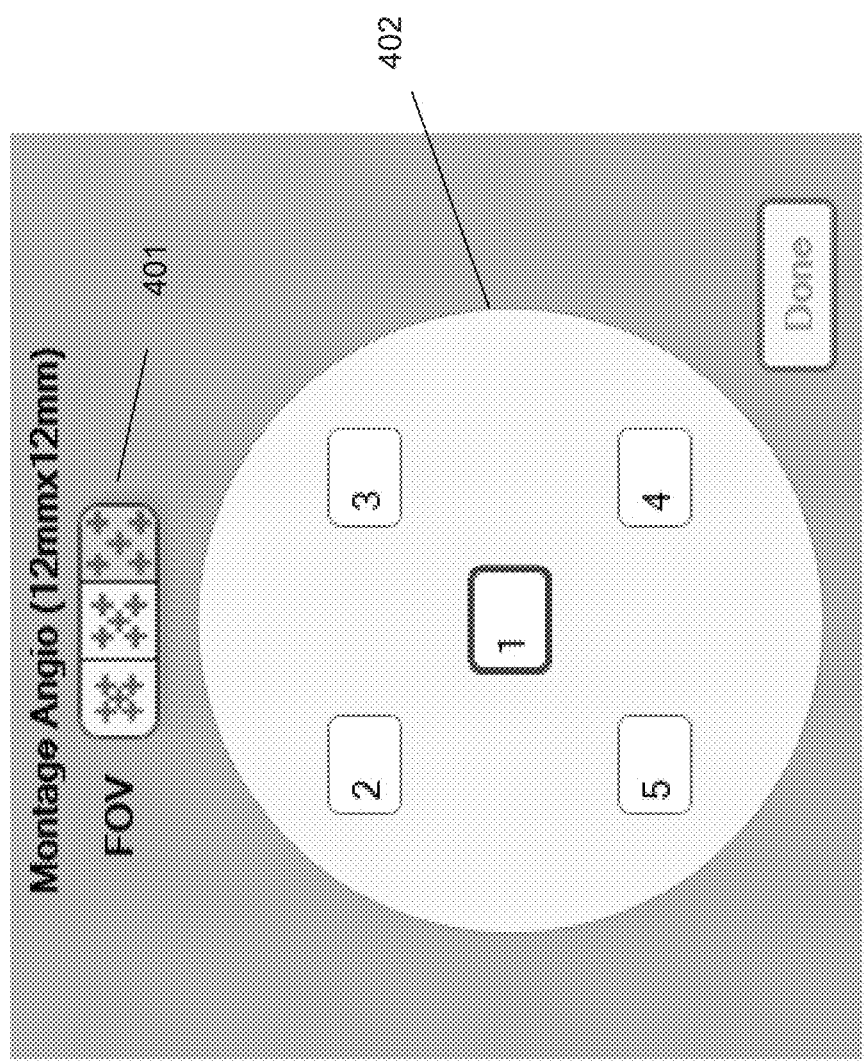
FIG. 4a illustrates an interface for accommodating variability in eye curvature while optimizing the field of view of a montage.

scans having predefined positions relative to each other, and which correspond to the five scan configuration of FIG. 4a.

Figure 5A:
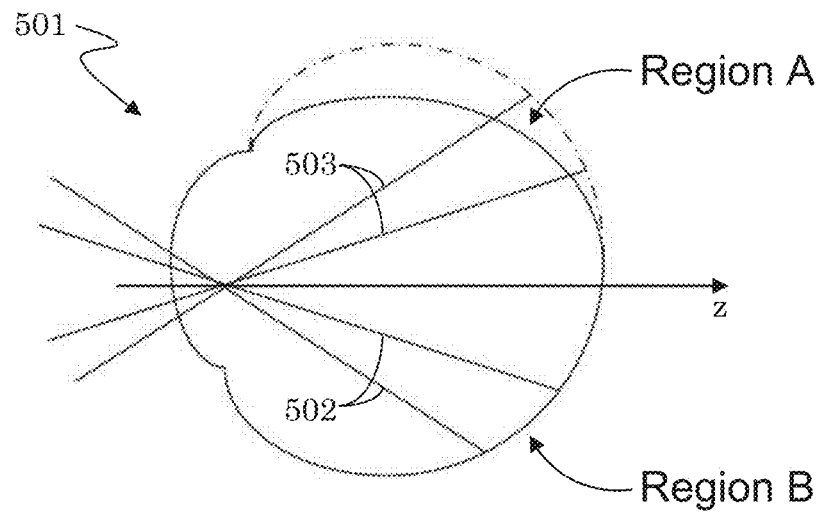
FIG. 5a illustrates an eye having a stronger curvature of the retina at a Region A as compared to a Region B.
Figure 5C:
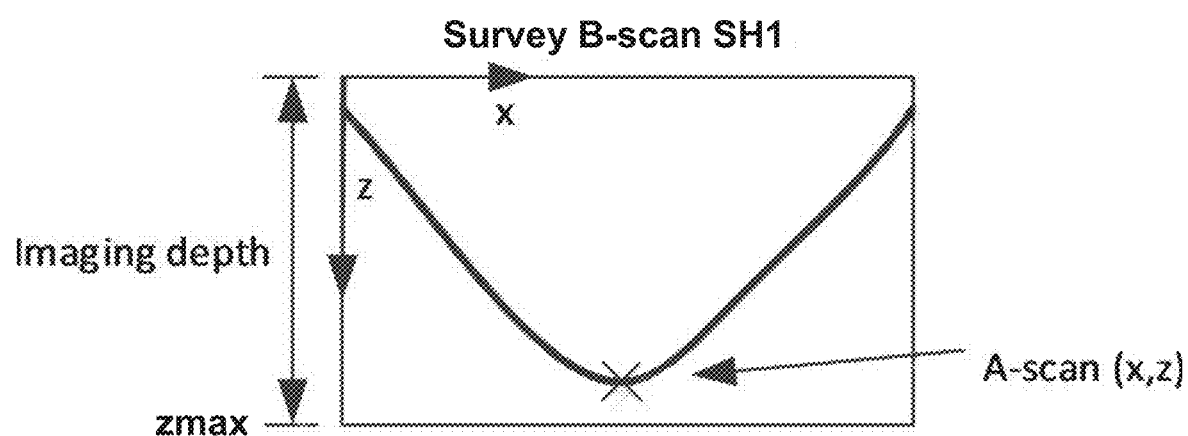
FIG. 5b illustrates a scan configuration (including prescans) to be applied to a scan option consisting of five (cube)

FIG. 5c illustrates how the depth coordinates of A-scans that comprise a survey B-scan (which may be part of a prescan) may be calculated to determine if B-scans in this area of the retina can be fully resolved within the imaging depth of the (OCT) instrument.

Figure 5B:
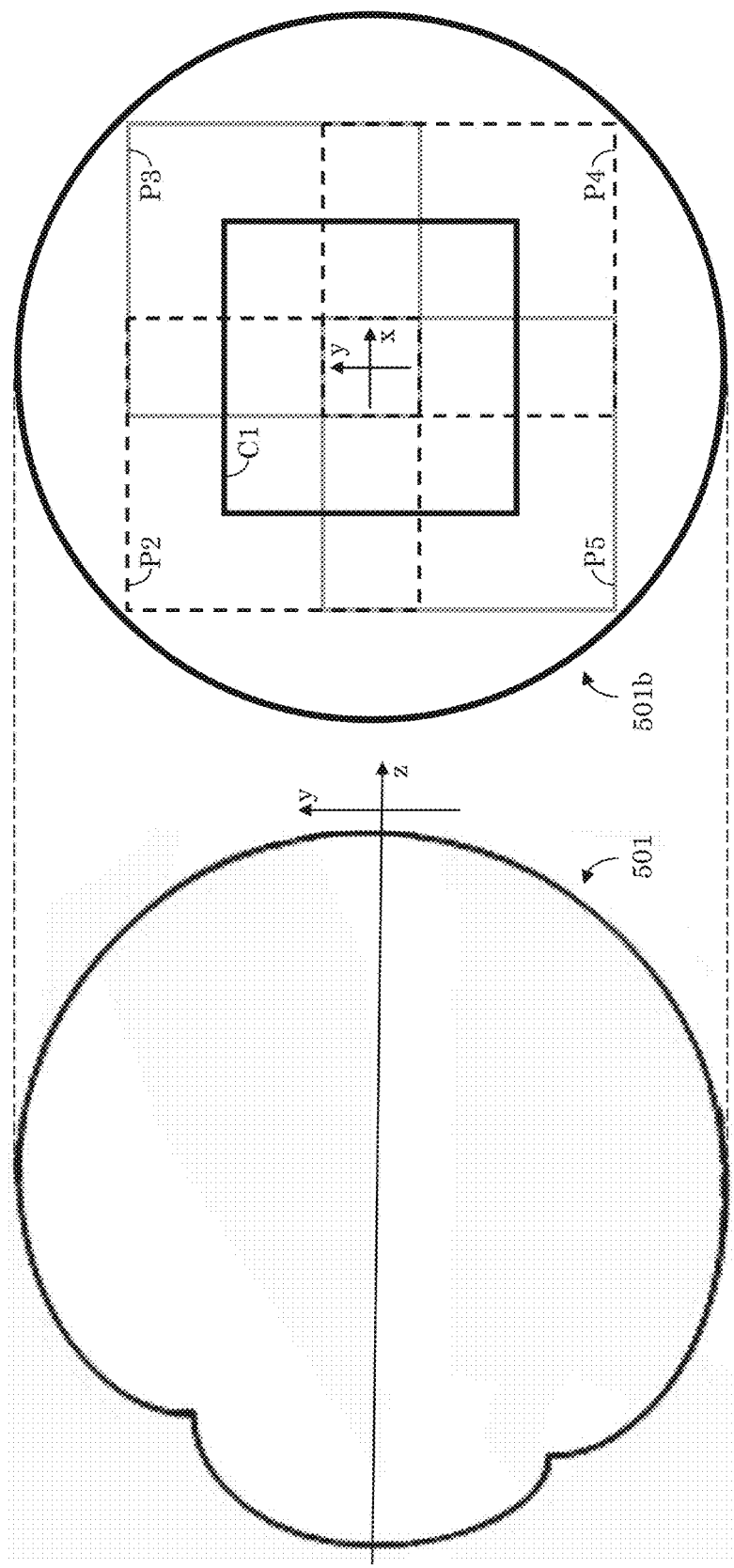
Figure 5B:
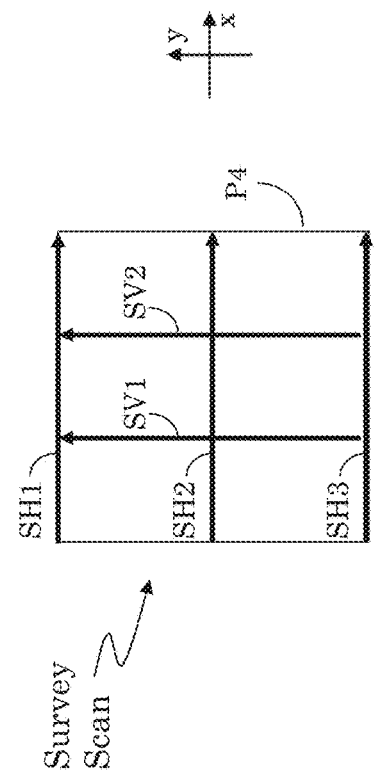
Figure 5D:
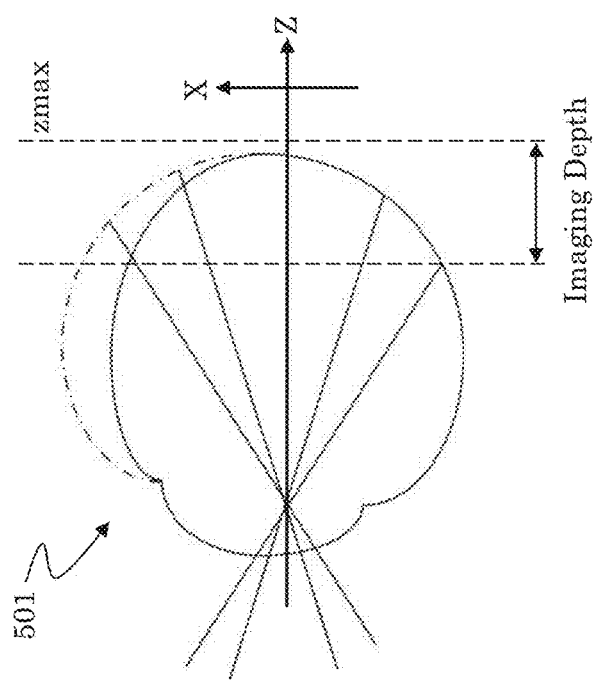
Figure 5D:
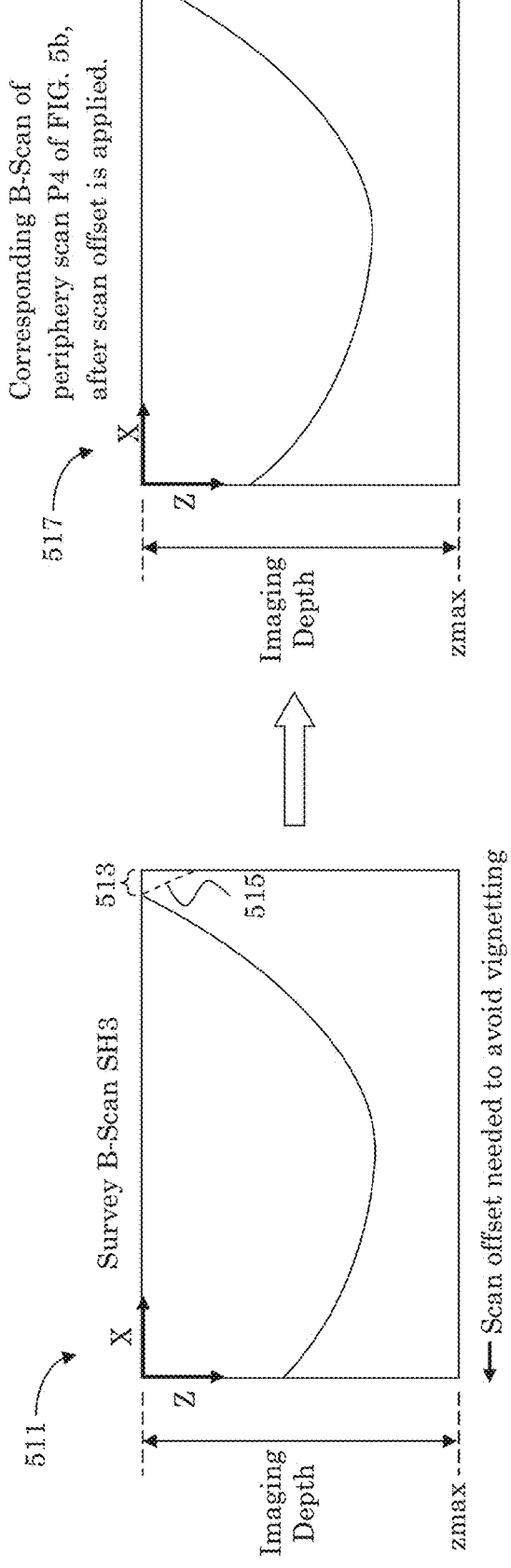

FIG. 5d illustrates a case where a scan region is offset (shifted) due to part of a survey B-scan not being fully resolved within the imaging depth of the instrument.

Figure 6A:
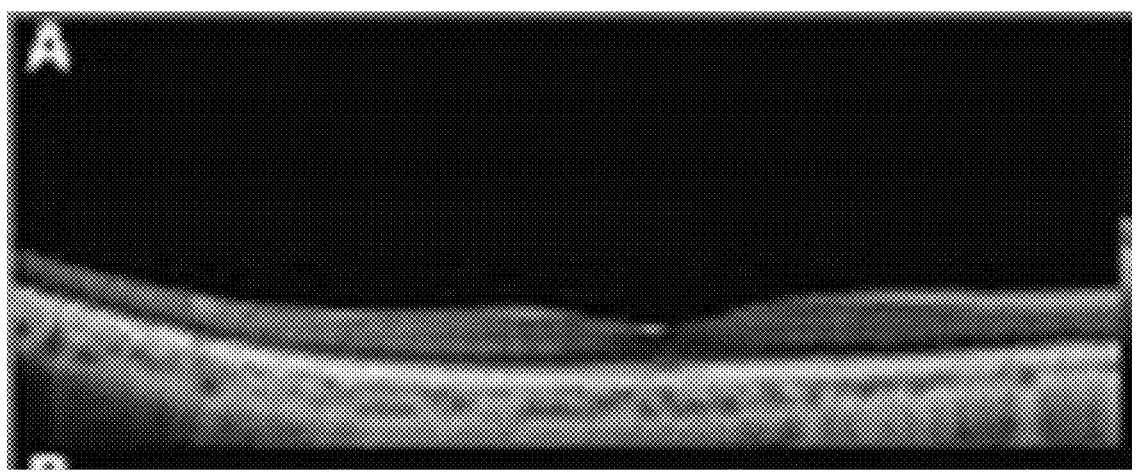

FIG. 6a is an example showing a wider field of view volume scan that collects all of the data over a flat area of retinal tissue with good resolution.

Figure 6B:

FIG. 6b illustrates an example requiring a larger number of volumes with smaller transverse field of views to fully capture the retinal tissue with high resolution due to the retinal tissue having substantially more curvature.

Figure 6C:
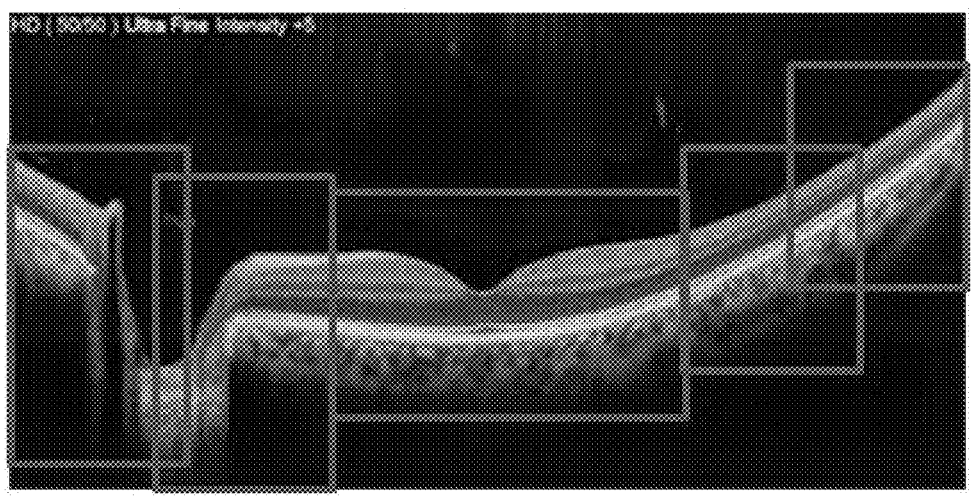

FIG. 6c shows, in two dimensions, the montaging of multiple retina samplings (scans) with different heights and widths, as indicated by highlighted rectangles.

Figure 6D:
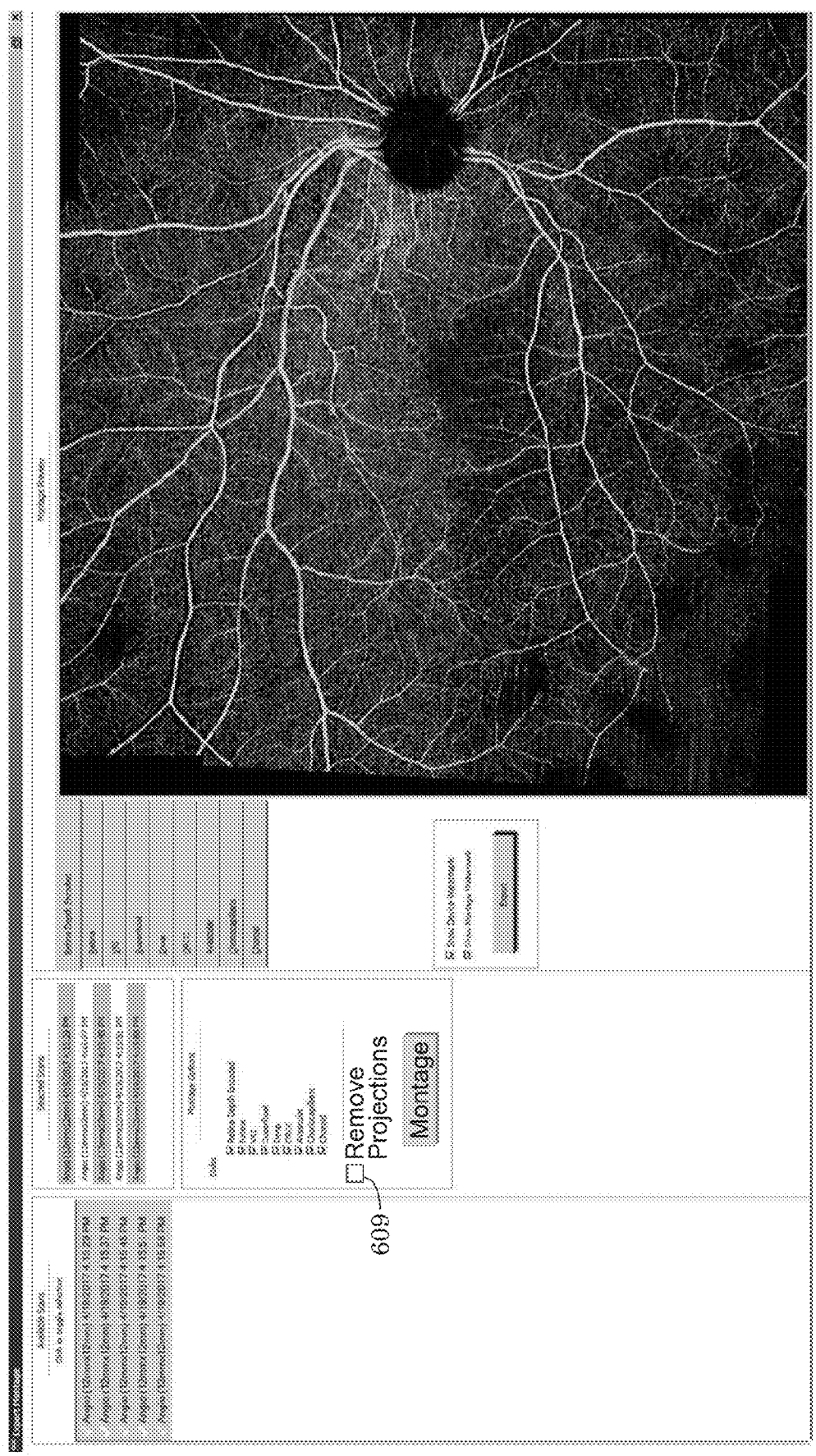

FIG. 6d shows a montaged image where flow projection artifact removal has not been enabled, in this case via selection of a selectable user input.

Figure 6E:
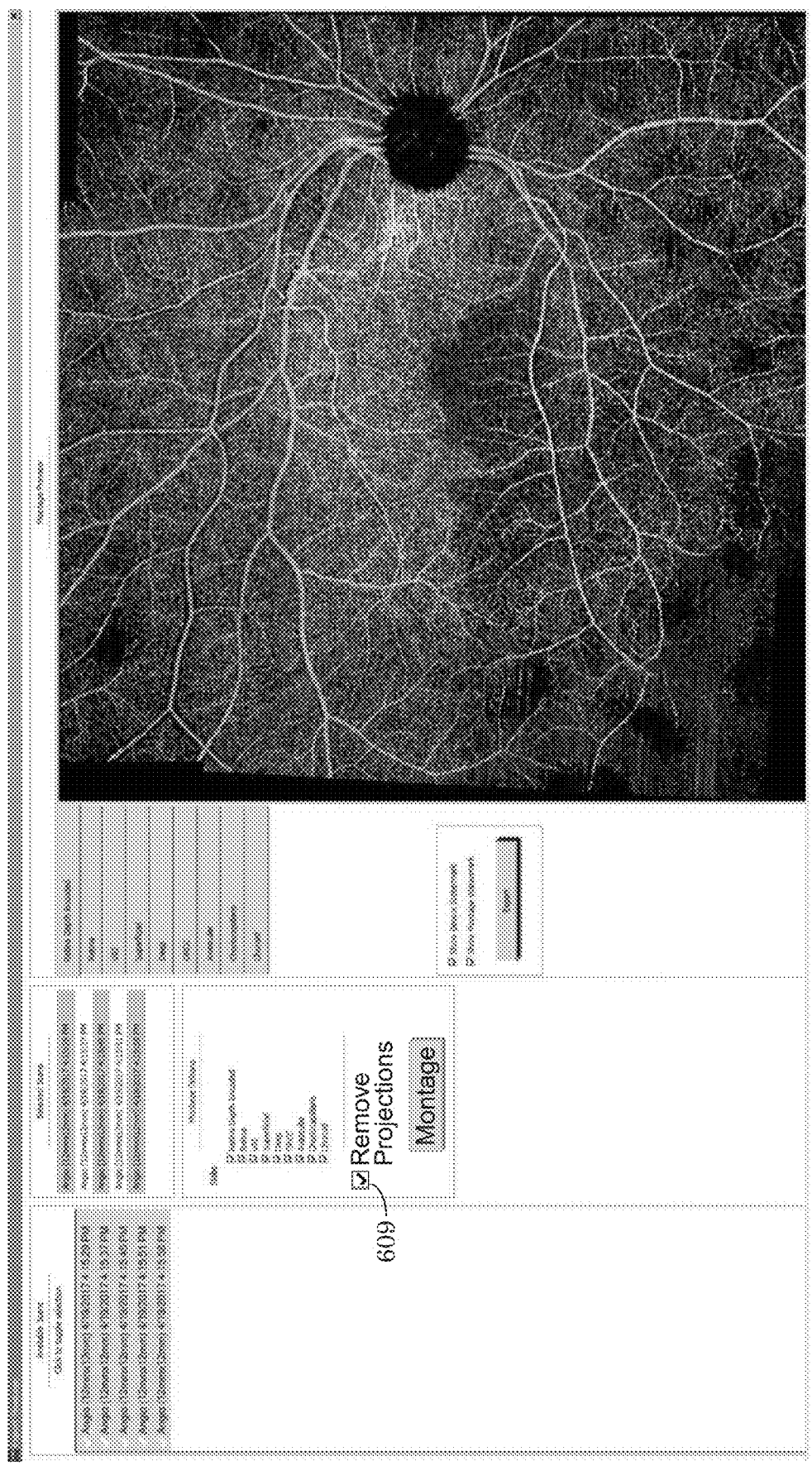

FIG. 6e shows a case where flow projection artifact removal has been enabled by mean of the selectable user input of FIG. 6d.

Figure 7A:
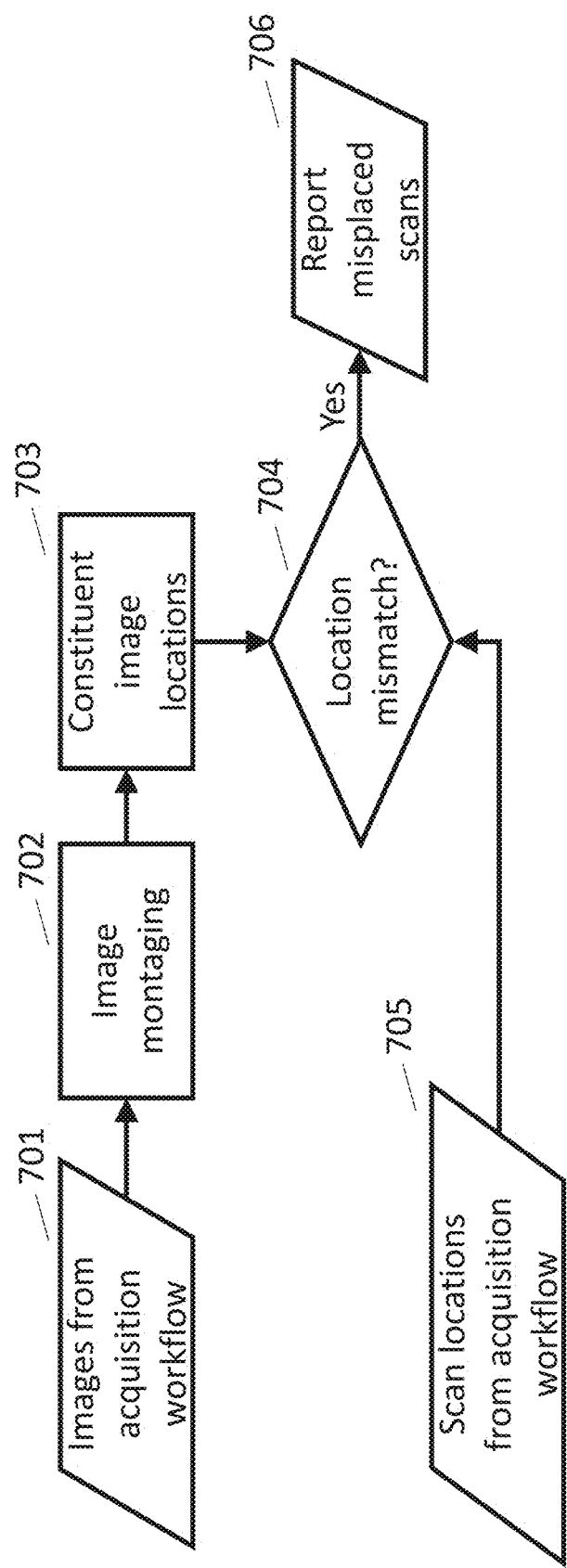

FIG. 7a illustrates a workflow for checking the locations of individual, constituent scans within a montage.

Figure 7C:
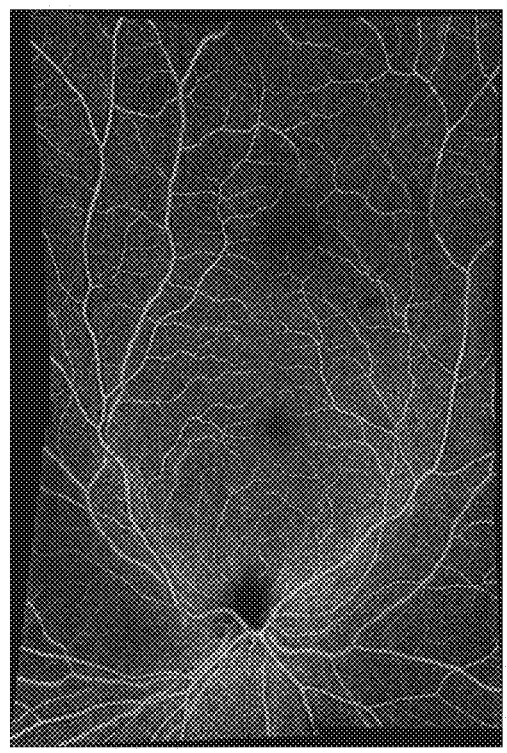
Figure 7B:
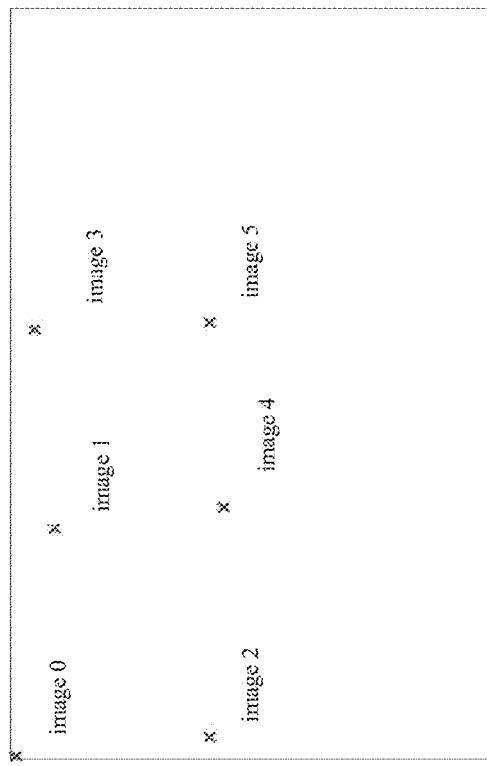

FIG. 7b illustrates the identifying of the locations of constituent images in a montaged image. For example, the locations may be identified by identifying a pixel number from each constituent image and locating that pixel in the composite, montaged image, where an "x" indicates specific pixel locations.

FIG. 7c illustrates a montaged image corresponding to the mapping of constituent images of FIG. 7b.

Figure 8:
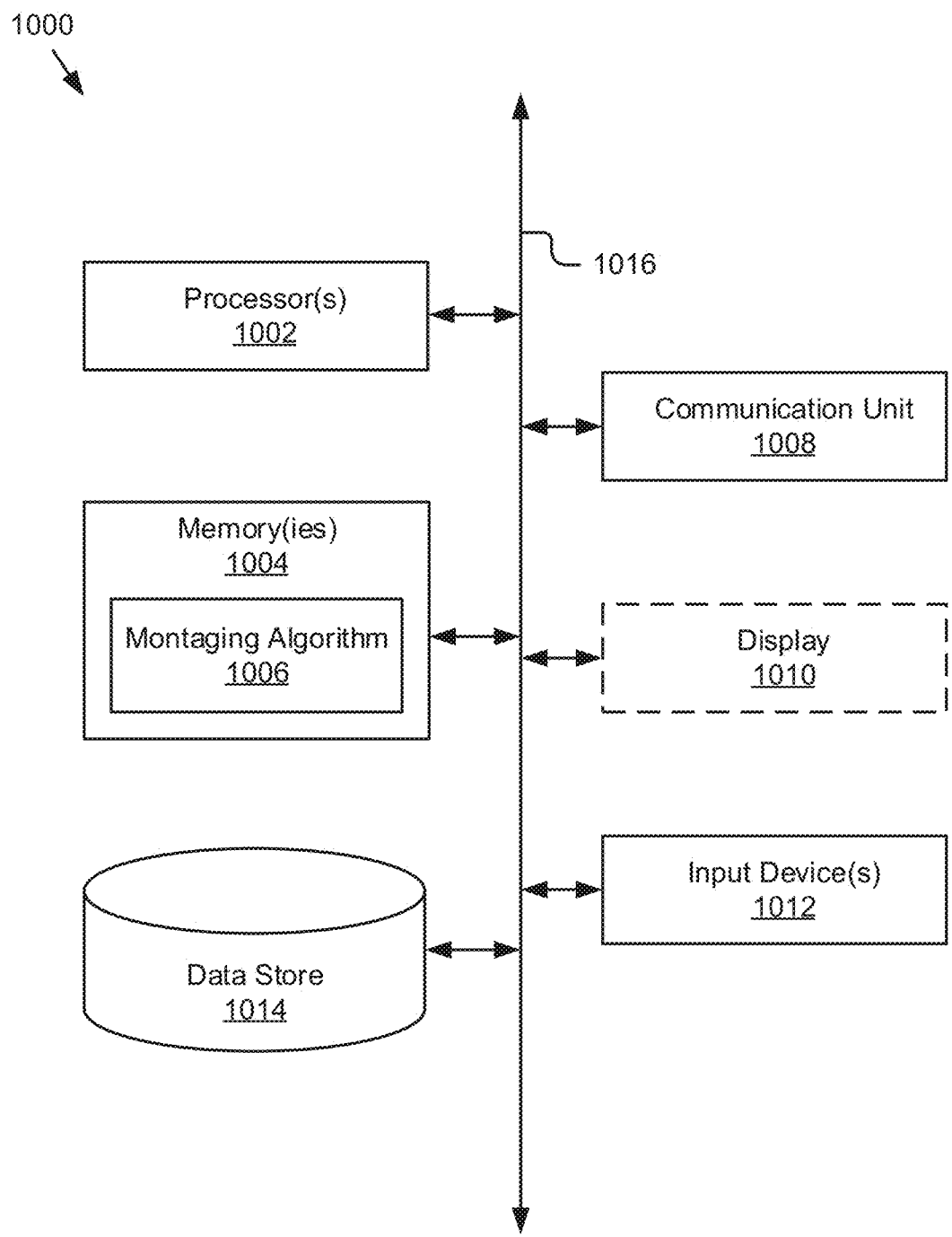

FIG. 8 illustrates a computer system suitable for use in various embodiments of the present invention.

DESCRIPTION OF THE PREFERRED EMBODIMENTS

All patent and non-patent references cited within this specification are herein incorporated by reference in their entirety to the same extent as if the disclosure of each individual patent and non-patient reference was specifically and individually indicated to be incorporated by reference in its entirely.

Example Optical Coherence Tomography (OCT) System

Figure 1:
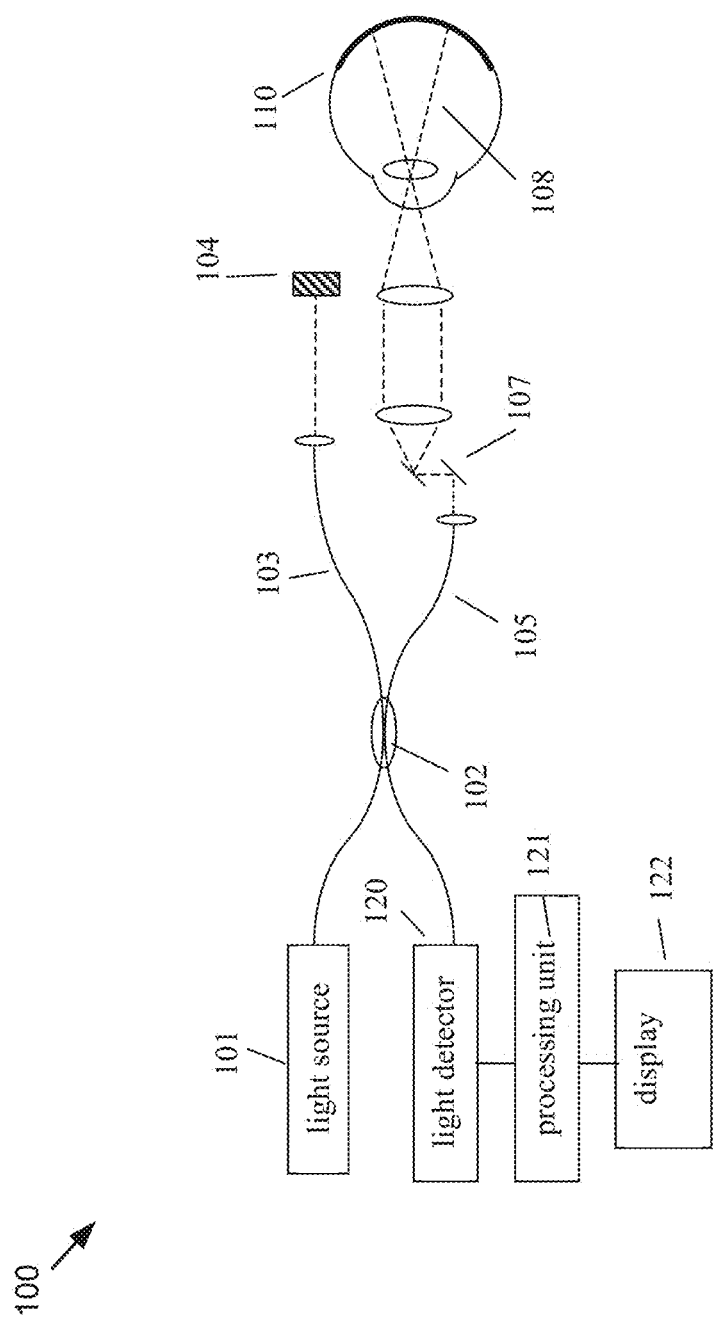
FIG. 1 illustrates a generalized FD-OCT system used to collect 3-D image data of the eye suitable for use with the present invention.

A generalized FD-OCT system used to collect 3-D image data of the eye suitable for use with the present invention is illustrated in FIG. 1. A FD-OCT system 100 includes a light source, 101. Typical light sources include, but are not limited to, broadband light sources with short temporal coherence lengths or swept laser sources. A beam of light from source 101 is routed, typically by optical fiber 105, to illuminate the sample 110, a typical sample being tissues in the human eye. The source 101 can be either a broadband light source with short temporal coherence length in the case of SD-OCT or a wavelength tunable laser source in the case of SS-OCT. The light is scanned, typically with a scanner 107 between the output of the fiber and the sample, so that the beam of light (dashed line 108) is scanned laterally (in x and y) over the region of the sample to be imaged. Light scattered from the sample is collected, typically into the same fiber 105 used to route the light for illumination. Reference light derived from the same source 101 travels a separate path, in this case involving fiber 103 and retro-reflector 104 with an adjustable optical delay. Those skilled in the art will recognize that a transmissive reference path can also be used and that the adjustable delay could be placed in the sample or reference arm of the interferometer. Collected sample light is combined with reference light, typically in a fiber coupler 102, to form light interference in a detector 120. Although a single fiber port is shown going to the detector, those skilled in the art will recognize that various designs of interferometers can be used for balanced or unbalanced detection of the interference signal. The output from the detector 120 is supplied to a processor 121 that converts the observed interference into depth information of the sample. The results can be stored in the processor 121 or other storage medium or displayed on display 122. The processing and storing functions may be localized within the OCT instrument or functions may be performed on an external processing unit (e.g., computer system 1000 shown in FIG. 8) to which the collected data is transferred. This unit could be dedicated to data processing or perform other tasks which are quite general and not dedicated to the OCT device. The processor 121 may contain for example a field-programmable gate array (FPGA), a digital signal processor (DSP), an application specific integrated circuit (ASIC), a graphics processing unit (GPU), a system on chip (SoC) or a combination thereof, that performs some, or the entire data processing steps, prior to passing on to the host processor or in a parallelized fashion. The display can be a traditional display or of the touch screen type and can include a user interface for displaying information to and receiving information from an instrument operator, or user. The user can interact with the display using any type of user input as known to those skilled in the art including, but not limited to, mouse, knobs, buttons, and touch screen.

The interference causes the intensity of the interfered light to vary across the spectrum. The Fourier transform of the interference light reveals the profile of scattering intensities at different path lengths, and therefore scattering as a function of depth (z-direction) in the sample. The profile of scattering as a function of depth is called an axial scan (A-scan). A set of A-scans measured at neighboring locations in the sample produces a cross-sectional image (tomogram or B-scan) of the sample. A collection of B-scans collected at different transverse locations on the sample makes up a data volume or cube. For a particular volume of data, the term fast axis refers to the scan direction along a single B-scan whereas slow axis refers to the axis along which multiple B-scans are collected. A variety of ways to create B-scans are known to those skilled in the art including but not limited to along the horizontal or x-direction, along the vertical or y-direction, along the diagonal of x and y, or in a circular or spiral pattern. A volume of 3D data can be processed to generate wide field fundus images (i.e., en face images) by assigning a single representative value for the intensity values (e.g. summation, integration, median value, minimum value, etc.) in all or a portion of the volume along an axis of the volume (see for example U.S. Pat. Nos. 7,301,644 and 8,332,016, both of which are hereby incorporated by reference in their entirety). These images may be referred to as slab images.

The sample and reference arms in the interferometer could consist of bulk-optics, fiber-optics or hybrid bulk-optic systems and could have different architectures such as Michelson, Mach-Zehnder or common-path based designs as would be known to those skilled in the art. Light beam as used herein should be interpreted as any carefully directed light path. In time-domain systems, the reference arm needs to have a tunable optical delay to generate interference. Balanced detection systems are typically used in TD-OCT and SS-OCT systems, while spectrometers are used at the detection port for SD-OCT systems. The invention described herein could be applied to any type of OCT system.

The above-described OCT employs a traditional point scanning, or flying spot, technique where a single point of light is scanned across the sample, typically in two dimensions. It is to be understood, however, that the OCT system may be modified to employ any number of other scanning techniques, including parallel techniques. In parallel techniques, a series of spots (multi-beam), a line of light (line-field), or a two-dimensional field of light (partial-field and full-field) is directed to the sample. The resulting reflected light is combined with reference light and detected. Parallel techniques can be accomplished in TD-OCT, SD-OCT or SS-OCT configurations. It is further to be understood that any scan manipulation (e.g., manipulation of cube scans, B-scans, and/or A-scans) described herein is compatible with any OCT scanning technique. Several groups have reported on different parallel FD-OCT configurations (Hiratsuka, H. et al., Opt. Lett. 23, 1420, 1998; Zuluaga, A. F. et al., Opt. Lett. 24, 519-521, 1999; Grajciar, B. et al., Opt. Express 13, 1131, 2005; Blazkiewicz, P. et al., Appl. Opt. 44, 7722, 2005; Povaay, B. et al., Opt. Express 14, 7661, 2006; Nakamura, Y. et al., Opt. Express 15, 7103, 2007; Lee, S.-W. et al., IEEE J. Sel. Topics Quantum Electron. 14, 50-55, 2008; Mujat, M. et al., Optical Coherence Tomography and Coherence Domain Optical Methods in Biomedicine XIII 7168, 71681E, 2009; Bonin, T. et al., Opt. Lett. 35, 3432-4, 2010; Wieser, W. et al., Opt. Express 18, 14685-704, 2010; Potsaid, B. et al., Opt. Express 18, 20029-48, 2010; Klein, T. et al., Biomed. Opt. Express 4, 619-34, 2013; Nankivil, D. et al., Opt. Lett. 39, 3740-3, 2014).

Furthermore, the OCT system may use any one of a number of OCT Angiography processing algorithms on OCT data collected at the same or approximately the same transverse locations on a sample at different times to identify and/or visualize regions of motion or flow. A typical OCT angiography data set contains multiple scans repeated at the same transverse locations. Motion contrast algorithms can be applied to the intensity information derived from the image data (intensity-based algorithm), the phase information from the image data (phase-based algorithm), or the complex image data (complex-based algorithm). An en face vasculature image is an image displaying motion contrast signal in which the data dimension corresponding to depth is displayed as a single representative value, typically by summing or integrating all or an isolated portion of the data as described above.

The OCT system discussed herein may provide 2D (i.e. cross-sectional) images, en-face images, 3-D images, metrics related to a health condition, and the like. This system may be used with any other system. The OCT system may be used to analyze any sample.

Example Slit Scanning Fundus Imaging System

Figure 2:
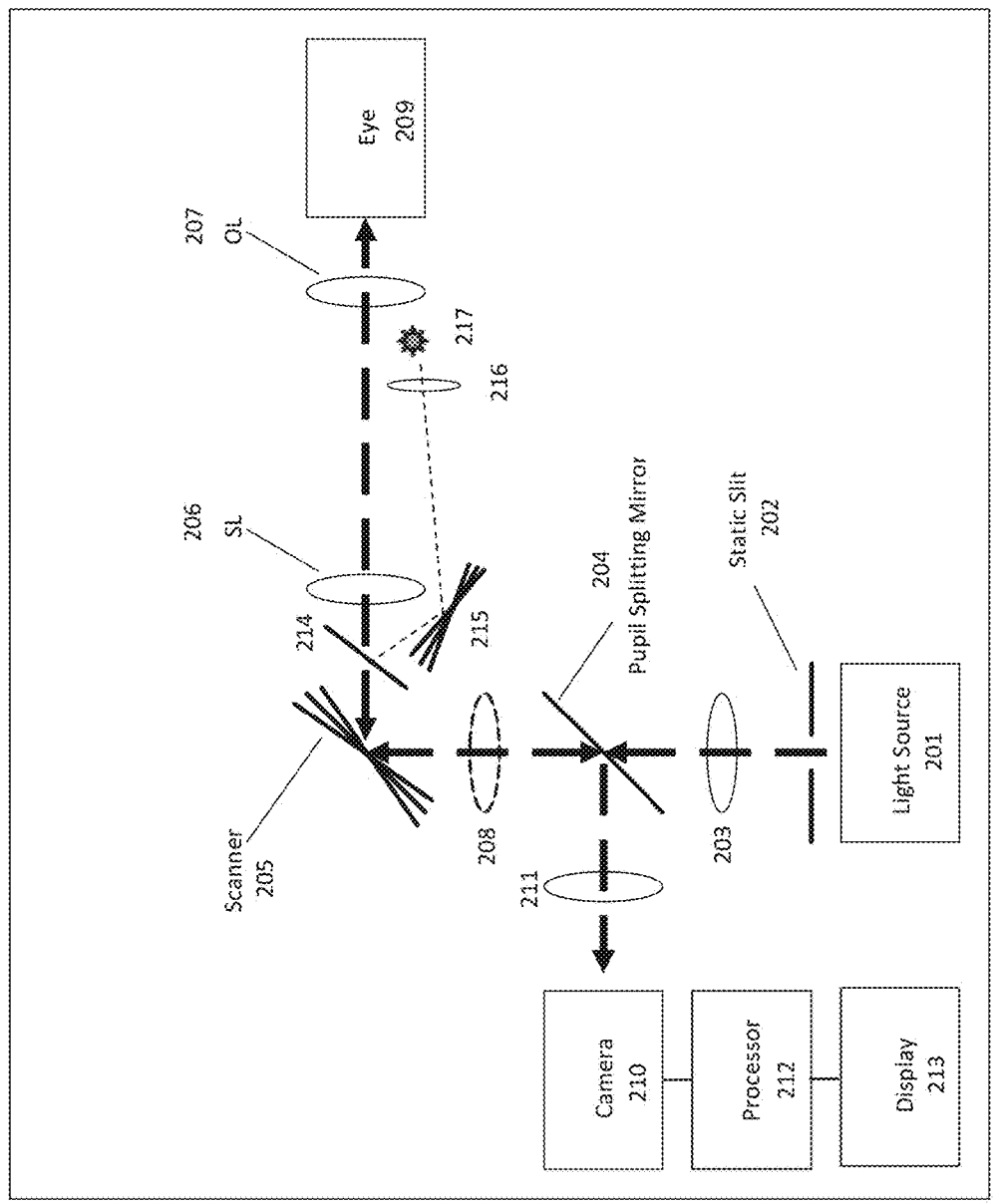
FIG. 2 illustrates an example of a slit scanning ophthalmic system suitable for collecting fundus images for use with aspects of the present application.

FIG. 2 illustrates one example of a slit scanning ophthalmic system suitable for collecting fundus images for use with aspects of the present application. As depicted, the system 200 includes one or more light sources 201, preferably a multi-color LED system or a laser system in which the etendue has been suitably adjusted. An adjustable slit 202 is positioned in front of the light source 201 to determine the illumination line width. This could also be established by the source independent of a slit or aperture. In the embodiment shown on FIG. 2, the slit 202 remains static during the imaging but can be adjusted to different widths to allow for different confocality levels and different applications either for a particular scan or during the scan for use in suppressing reflexes. An objective lens 203 forms a pupil of the slit. The objective lens 203 can be any one of state of the art lenses including but not limited to refractive, diffractive, reflective, or hybrid lenses/systems. The light passes through a pupil splitting mirror 204 and is directed towards a scanner 205. It is desirable to bring the scanning plane and the pupil plane as near together as possible to reduce vignetting in the system. Optional optics 208 may be included to manipulate the optical distance between the images of the two components. The main task of the pupil splitter 204 is to combine and split the illumination and detection beams and to aid in the suppression of system reflexes. The scanner 205 could be a rotating galvo scanner or other types of scanners (i.e. piezo or voice coil). Depending on whether the pupil splitting is done before or after the scanner 205, the scanning could be broken into two steps wherein one scanner is in the illumination path and a separate scanner is in the detection path. Specific pupil splitting arrangements are described in detail in US Patent Publication No. 2015/0131050, the contents of which are hereby incorporated by reference).

From the scanner, the light passes through one or more optics, in this case a scanning lens (SL) 206 and an ophthalmic or ocular lens (OL) 207, that allow for the pupil of the eye 209 to be imaged to an image pupil of the system. One possible configuration for these optics is a Kepler type telescope wherein the distance between the two lenses is selected to create an approximately telecentric intermediate fundus image (4-f configuration). The ophthalmic lens 207 could be a single lens, an achromatic lens, or an arrangement of different lenses. All lenses could be refractive, diffractive, reflective or hybrid as known to one skilled in the art. The focal length(s) of the ophthalmic lens 207, scan lens 206 and the size and/or form of the pupil splitting mirror 204 and scanning mirrors 205 could be different depending on the desired field of view (FOV), and so an arrangement in which multiple components can be switched in and out of the beam path, for example by using a flip in optic, a motorized wheel, or a detachable optical element, depending on the field of view can be envisioned. Since the field of view change results in a different beam size on the pupil, the pupil splitting can also be changed in conjunction with the change to the FOV. It is possible to have a 45°-60° field of view as is typical for fundus cameras. Higher fields of view (60°-120°) may be desired for a combination of the Broad-Line Fundus Imager (BLFI) with other imaging modalities such as optical coherence tomography (OCT). The upper limit for the field of view will be determined by the accessible working distance in combination with the physiological conditions around the human eye. Because a typical human retina has a FOV of 140° horizontal and 80°-100° vertical, it may be desirable to have an asymmetrical field of view for the highest possible FOV on the system.

The light passes through the pupil of the eye 209 and is directed towards the retinal surface. The scanner 205 adjusts the location of the light on the retina or fundus such that a range of transverse locations on the eye are illuminated. Reflected or scattered light (or emitted light in the case of fluorescence imaging) is directed back along the same path as the illumination. At the pupil splitting mirror 204, the reflected light is separated from the illumination light and directed towards a camera 210. An objective lens 211 exists in the detection path to image the fundus to the camera 210. As is the case for objective lens 203, objective lens 211 could be any type of refractive, diffractive, reflective or hybrid lens as is known by one skilled in the art. Additional details of the scanning, in particular, ways to reduce artifacts in the image, are described in PCT Publication No. WO2016/124644, the contents of which are hereby incorporated by reference.

The camera 210 is connected to a processor 212 and a display 213. The processing and displaying modules can be included with the system 200 itself or on a dedicated processing and displaying unit, such as a computer system wherein data is passed from the camera 210 to the computer system over a cable or network including wireless networks. The display and processor can be an all in one unit. The display can be a traditional display or of the touch screen type and can include a user interface for displaying information to and receiving information from an instrument operator or user. The user can interact with the display using any type of user input as known to those skilled in the art including, but not limited to, mouse, knobs, buttons, and touch screen.

It is desirable for the patient's gaze to remain fixed while imaging is carried out. One way to achieve this is to provide a fixation target that the patient can be directed to stare at. Fixation targets can be internal or external to instrument depending on what area of the eye is to be imaged. One embodiment of an internal fixation target is shown in FIG. 2 for a slit scanning system. The same concept can be applied to the OCT system in FIG. 1. In addition to the primary light source 201 used for imaging, a second optional light source 217, such as one or more LEDs, can be positioned such that a light pattern is imaged to the retina using lens 216. A scanning element 215 can be positioned such that it is located at the pupil plane of the system so that the pattern on the retina can be moved depending on the desired fixation location. When montaging fundus images, it is necessary to change the rotation of the eye relative to the instrument and collect two or more images at different rotations. This is most easily accomplished by adjusting the fixation location in the system.

In the configuration shown in FIG. 2, scattered light returning from the eye 209 (e.g., a collection beam) is "descanned" by scanner 205 on its way to pupil splitting mirror 204. That is, scanner 205 scans the illumination beam from pupil splitting mirror 204 to define a scanning illumination beam across eye 209, but since it also receives returning light from eye 209 at the same scanning position, scanner 205 has the effect of descanning the returning light (e.g., cancelling the scanning action) to define a non-scanning (e.g., steady or stationary) collection beam sent to pupil splitting mirror 204, which in turn folds the collection beam toward the camera 210. Thus, the collection beam (from all scan positions of the scanning illumination beam) is applied to the same sensor region of the camera 210. A full-frame image may be built up (e.g., in processor 212) from a composite of the individually captured collection beams (resulting from the scanning illumination beam), such as by montaging, or stitching. However, other scanning configuration are also contemplated, including ones where the illumination beam is scanned across the eye 209 and the collection beam is scanned across a 2D-area photosensor array of the camera. PCT Publication WO 2012/059236 and US Patent Publication No. 2015/0131050, hereby incorporated by reference, describe several embodiments of slit scanning ophthalmoscopes including other designs where the light is swept across the camera, and also descanned imaging schemes. While the detailed description is focused on slit scanning ophthalmoscopes, many of the system elements described herein, in particular the user interface elements, could have applicability to any type of ophthalmic imaging and diagnostic systems.

Montage Workflow for Minimized Chin Time

Figure 3A:
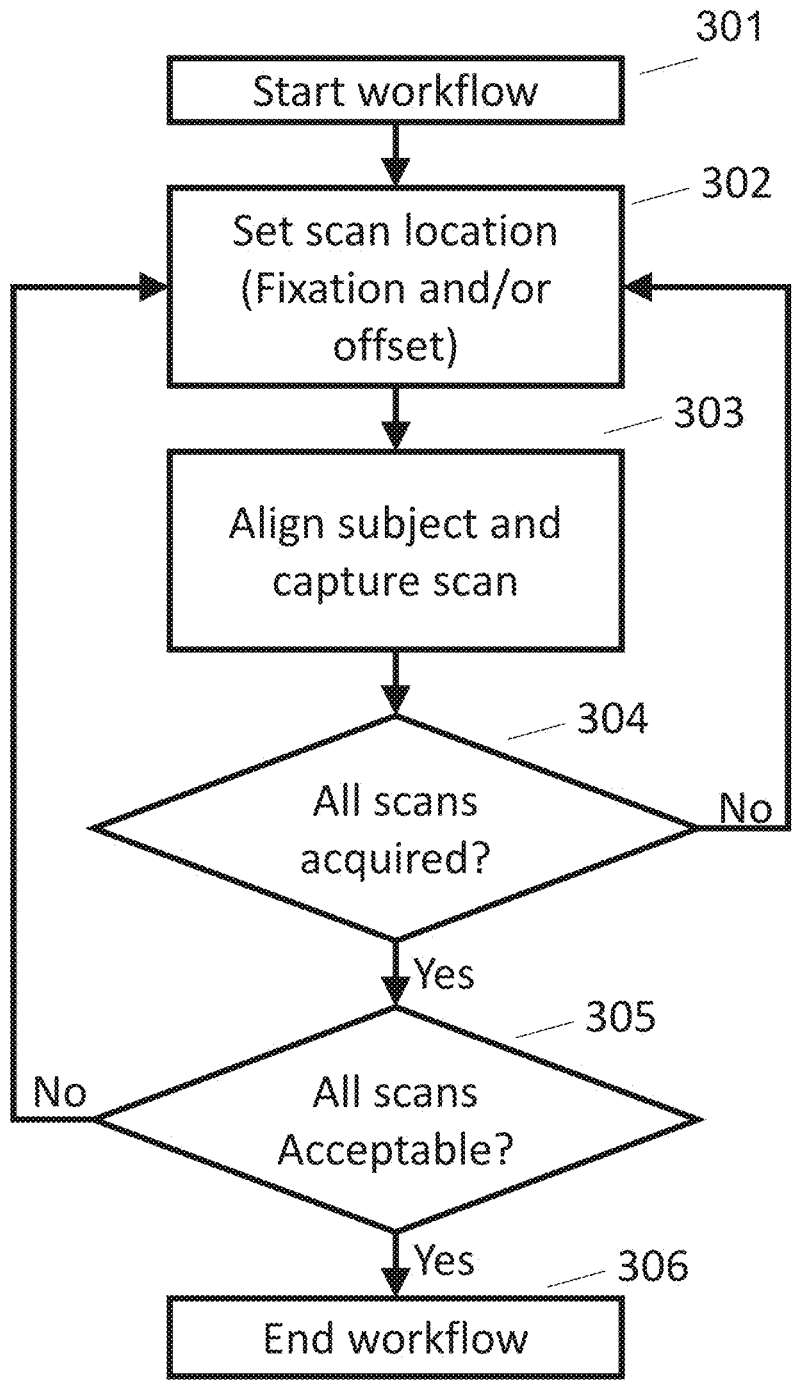
FIG. 3a illustrates an example acquisition workflow for collecting images for montaging using an ophthalmic imaging system, such as the OCT system of FIG. 1 or the fundus imaging system of FIG. 2.

FIG. 3a illustrates one potential acquisition workflow for collecting the images for a montaged fundus image using any type of ophthalmic imaging system, for example the OCT system illustrated in FIG. 1 or the fundus imaging system illustrated in FIG. 2, among others, that is designed to minimize the patient chin time (the time it takes to acquire all necessary scans for a montage). In this embodiment, the acquisition workflow may be started (301) by the system operator for example by selection of a particular scan option from a user interface that provides one or more scan options, or automatically by the software upon detection of an eye within its view. Subsequently, the system sets the scan location (302) by adjusting either the fixation location or scan offset or both according to a pre-defined arrangement for a particular scan option. The arrangement may consist of at least two scans of the same or different field of views covering different transverse locations on the retina but containing some overlapping portion. The scans may span similar or different size areas. At this point, the patient may optionally be more carefully aligned (or realigned) to the instrument, either manually by the operator or using an automatic alignment by the system and the scan capture may be performed (303) manually or by means of an assisted software. The workflow may perform steps 302 and 303 until all pre-defined scans (e.g., needed for creation of a montaged image) are acquired (304). Once completed (e.g., step 304=Yes), the instrument operator may be presented with all (or a select group of) scans (305) in one or more scan quality check screens where poor quality scans may be identified either manually upon visual review by the user or automatically using a quality assessment algorithm, which may determine a numerical quality factor for each scan. Any unacceptable (e.g., poor quality scans) may be re-captured (step 305). This may effectively create a confidence interval for each constituent image to be reviewed and designated for rescanning, if necessary. The workflow may repeat steps 302, 303, and 304 on those pre-identified scans. Once all presented scans are acceptable (step 305), the operator or software may end the workflow (306), and the acquired scans can be montaged together using any of the many well-known feature matching and blending approaches (see for example Brown et al. "Recognising panoramas", In Proceedings of the 9th International Conference on Computer Vision, Volume 2, pages 1218-1225, Nice, October 2003; Brown et al. "Automatic Panoramic Image Stitching using Invariant Features", D. G. Int. J Comput Vision (2007) 74: 59; Shi et al. "Good Features to Track", Proceedings of the 9th IEEE Conference on Computer Vision and Pattern Recognition, Seattle, Springer, June 1994 hereby incorporated by reference). For OCT data, the first step would typically be to generate one or more en face images from each set of scan data (e.g., set of OCT scans that define a cube scan, or volume), and registering and/or montaging the en face images to each other. The en face images could be of the entire volume of data or particular slabs within the volume data, as is well known in the art. Automatically creating a composite montage from overlapping images typically involves several steps:

1) Detect features and calculate descriptors for them.
2) Match features among the images.
3) Calculate initial transformations ('homographies') between pairs of images that map the matching features onto each other.

4) Calculate an optimum set of homographies that provide the best matching among all of the images simultaneously ('bundle adjustment').
5) Calculate the best locations for the transitions among the constituent images in the final montage ('seaming').
6) Smoothly transition from each image to the others to reduce obvious boundaries ('blending').

Prior to these steps, distortion correction could be implemented which may involve using a projection removal algorithm as discussed in more detail below.

In some embodiments, each scan may contribute an equal amount, or a fixed region, to the montage. Alternatively, the determined numerical quality factor of each scan may be used to determine how much each scan contributes to the final montage. This may help improve the quality of the overall montaged image.

It is important to have good quality constituent scans (images) to create good montages. Poor quality scans (images) may result in poor overall montages that may be of limited use to a clinician/operator. Having a confidence interval for imaging/scanning would be beneficial for the operator (or technician) collecting the images and would provide an opportunity to determine whether an image should be taken again. A montaged image would also benefit from an algorithm, or process, that incorporates more of the better image(s) into the montage. For example, images that have clearer-looking regions of interest, such the macula or optic nerve, may be selected to contribute those clear-looking regions into the montaged image. In this way, the montage would have the best focused macula, optic nerve and other lesions of interest.

Figure 3B:
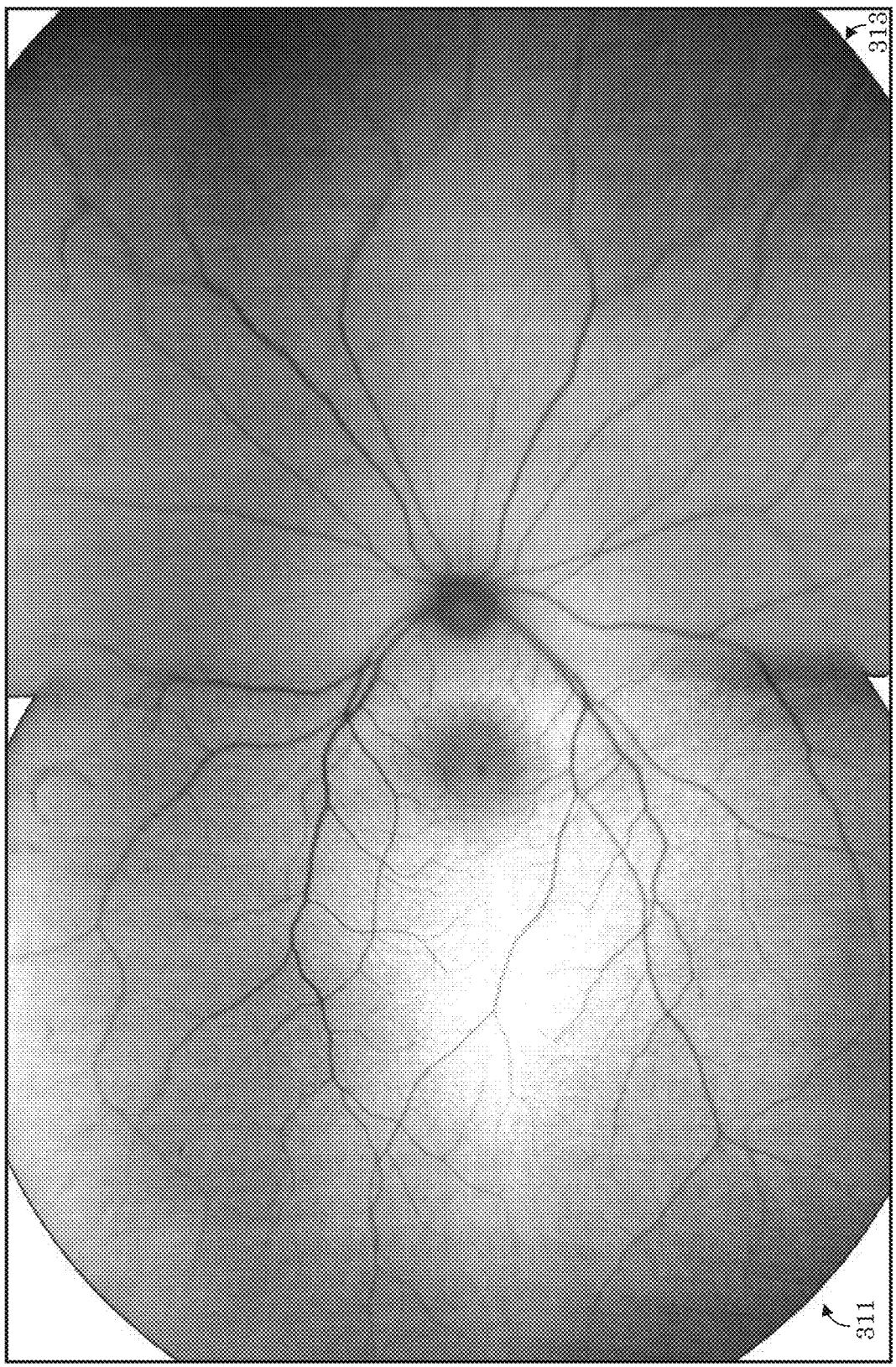
FIG. 3b illustrates a montaged image comprised of two constituent scans (images) of different quality, where equal amounts of each constituent image are stitched into the montaged image irrespective of their respective image quality.

FIG. 3b illustrates a montage of two scans 311 and 313 of different quality, where equal amounts of each image are stitched into the montage irrespective of their respective quality. In this approach, equal amounts of two, four, or more images contribute to a montage no matter how poor the constituent images may be. The constituent image 311 on the left shows choroidal detail whereas the constituent image 313 on the right does not show this detail and presents the optic nerve as very blurry.

Figure 3C:
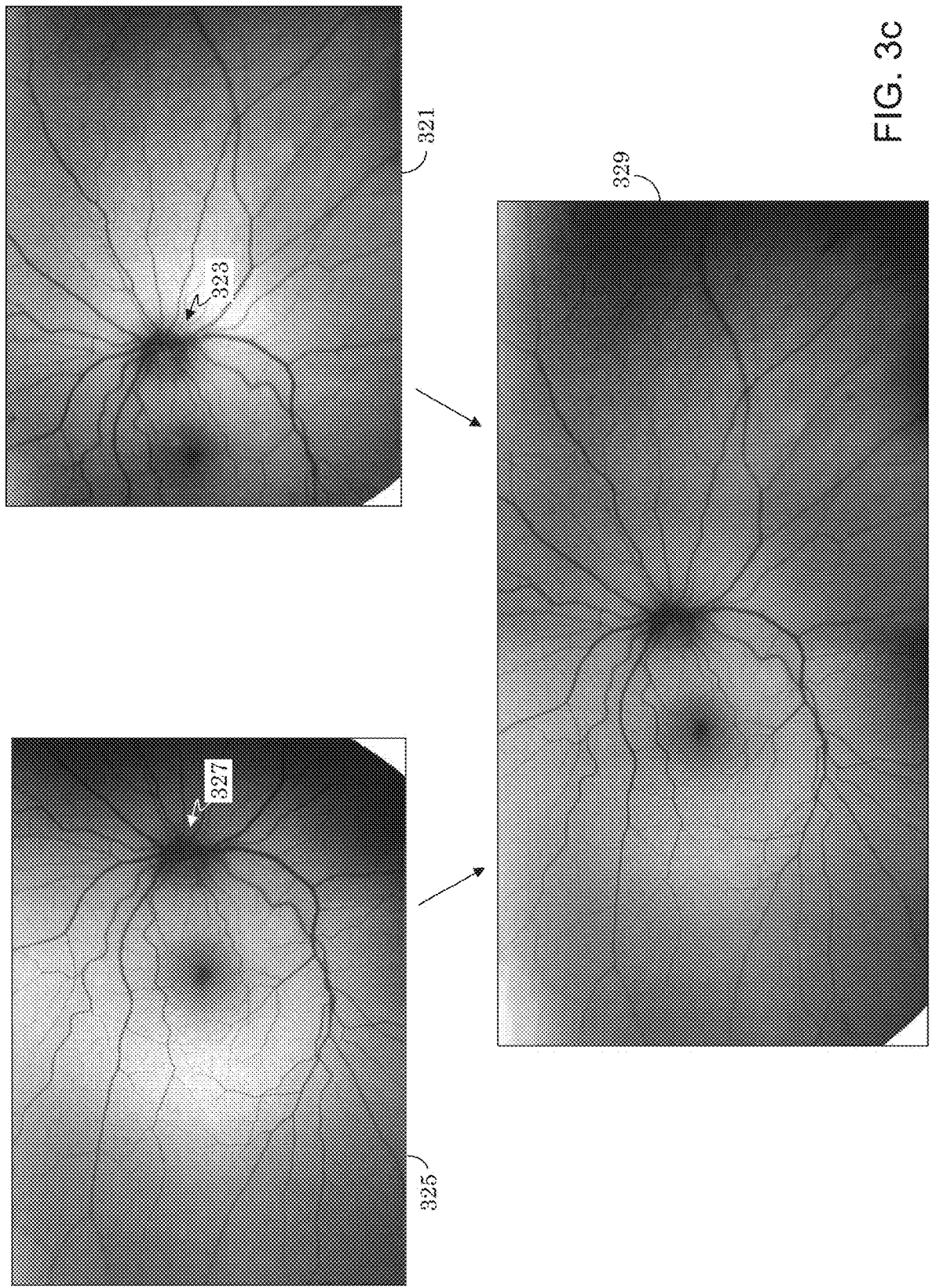
FIG. 3c shows another example of montaging two images.

Another example of montaging two images with equal weighting is shown in FIG. 3c. In this case, a first scan 321 on the right has a blurry optic nerve 323, and a second scan 325 on the left has a less blurry optic nerve 327. Ideally, one should use the less blurry optic nerve 327 from the second scan 327 in the construction of a montage, but since in the present embodiment the final montage 329 uses equal amounts from each scan 321 and 325, the final montage 329 shows good choroidal detail but a blurry optic nerve, which is contributed from image 321.

In a preferred embodiment, upon collecting an image (e.g., taking a photo or finishing a cube scan of a predefined region), a quality factor would be determined and displayed. For example, the quality factor may be given a numerical value from 1 to 10. Various techniques for assigning a quality factor, or measure, to an image are known in the art, and its particular implementation is not critical to the present invention. An example of assigning a quality metric to an image is described in U.S. Pat. No. 9,778,021, incorporated herein in its entirety by reference. If the quality factor is less than a predefined minimum (e.g., 6 out of 10), it would be advisable to re-do the image. For example, the display may provide an indicator identifying the bad image and suggesting that it be rescanned, or the algorithm may automatically rescan any image whose quality factor is less than a minimum, unless otherwise instructed by the operator. In this manner, poor quality montages may be avoided, or minimized. Additionally, the quality factor may be used to allocate contributions from each of the constituent scans to the final montaged image. For example, the algorithm may use more of the better quality constituent scan(s) (as determined by a higher value quality factor) to make the montaged image, rather than blindly stitching together the nasal and the temporal constituent images irrespective of whether one is of poorer quality than the other.

Figure 3D:
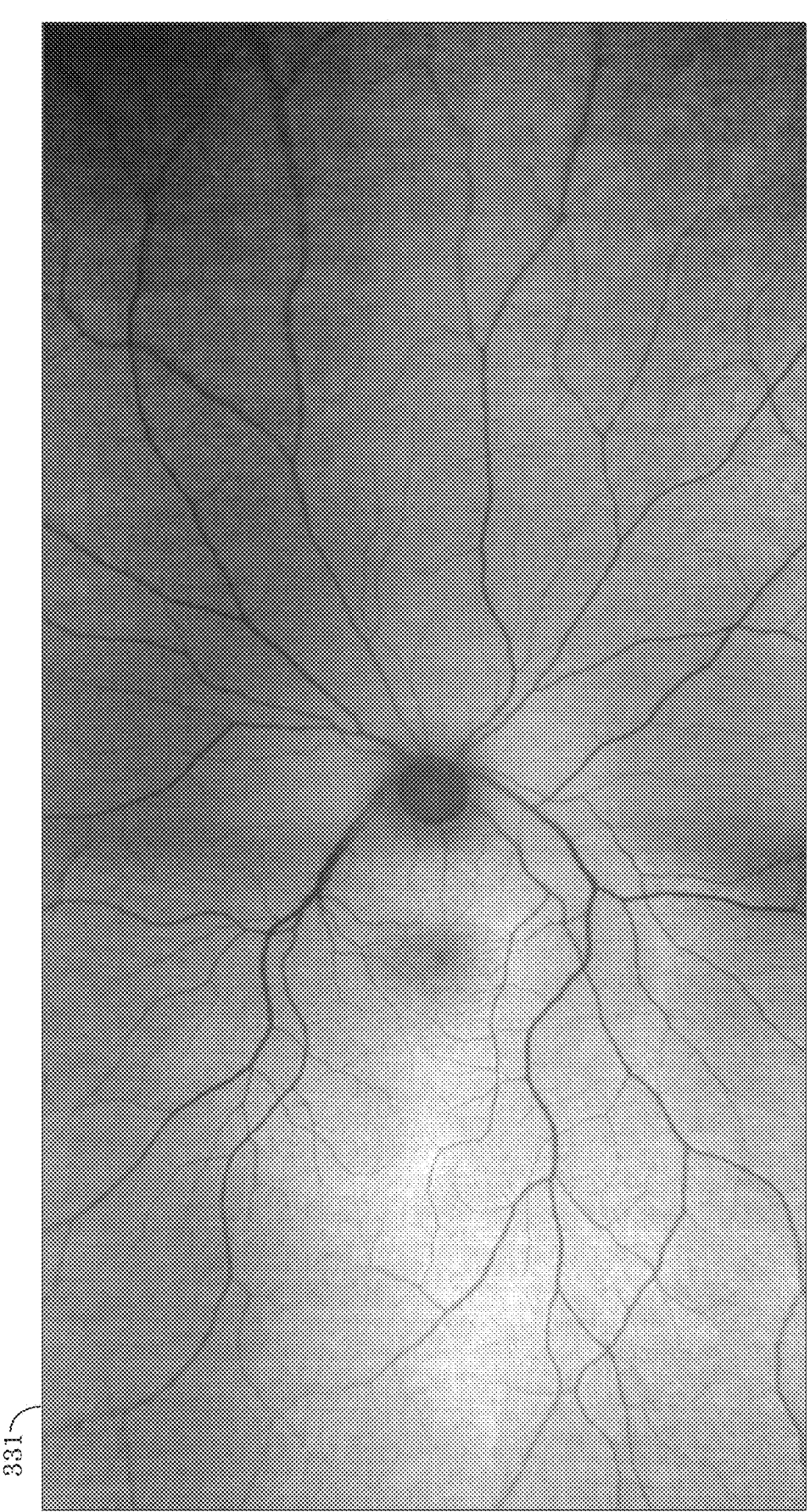
FIG. 3d illustrates a scan that incorporates more of a higher quality scan than a lower quality scan.

FIG. 3d illustrates a scan 331 that incorporates more of a higher quality scan than a lower quality scan. As shown, the choroidal detail is good throughout the montage, and both the optic nerve and macula are clear.

Curvature Considerations for OCT Montaging

The imaging depth of most standard OCT instruments is typically limited to 3 mm. Since the goal of montaging is to obtain a wide field of view, the montage workflow would ideally consist of acquiring a number of sets of OCT scan data (e.g., cube scans) placed as far as possible from each other so as to cover the widest field of view supported by the instrument while still having some overlap among the sets of OCT scan data. As the retinal curvature varies across the population, with high myopic eyes having stronger retinal curvature compared to emmetropic and hyperopic eyes, it would be more challenging to acquire an OCT cube scan at the peripheral region of the retina of a high myopic eyes without vignetting the B-scans. The optimal placement of the constituent scans of a montage would be different for a high myopic as compared to a hyperopic eye. Therefore, it is desirable to have different montage configurations available in an instrument to accommodate the variability in the eye's curvature across the population such as to optimize the field of view of the montage.

FIG. 4a illustrates an interface for accommodating variability in eye curvature while optimizing the field of view of a montage. In this embodiment, an OCT Angiography montage is desired. Three different FOV indicating icons 401 (each of which defines a different scan option) are presented to the user where "+" signs are used to indicate the (e.g., central) location of the multiple cube scans relative to each other within each scan option. Closely placed "+" signs indicate more tightly packed constituent scans (e.g., cube scans) having higher amounts of overlap between them. It is noted that the constituent cube scans within a scan option may be of different sizes and/or different resolutions. In the present example, the FOV indicating icon 401 on the far left indicates the most densely spaced cube scans, such as may be used for a highly myopic patient (e.g., to reduce vignetting of B-scans) to obtain a better quality, but smaller size, montaged image. The other two of the three FOV indicating icons 401 indicate a more spread out spacing of the cube scans, such as for use with eyes with larger curvatures.

As stated above, the "+" signs of the three FOV indicating icons 401, each indicates a relative location of multiple (e.g., five) scans, e.g., cube scans. Region 402 of the user interface 400 identifies each cube scan (e.g., scan icons 1 to 5, which may further indicate the sequence in which each cube scan is collected) and may illustrate the positioning of the cube scans relative to each other. For example, scan icon 1 may correspond to a central (cube) scan, and scan icons 2, 3, 4 and 5 may each correspond to a peripheral (cube) scan (e.g., peripheral to central scan 1). Optionally, the relative position of any of the scans indicated in interface 400 may be individually adjusted relative to each other. Individual scan icons may be automatically adjusted, as explained below, and/or may be manually adjusted by dragging the position of any of the scan icons 1 to 5 to a new relative position within region 402 by use of a user input device, e.g., a mouse pointer. It may be desirable to adjust the relative position of any scan (beyond the default, relative positions of any given scan option 401) if, for example, it is found that a particular scan is of lower than desired quality or partially failed (e.g., due to excessive curvature in the eye within the region of the failed scan). In this case, the undesired scan may be replaced by a higher quality scan by moving the location of the scan to a less curved section of the eye, such as closer to the central area of the eye.

Since the multiple cube scans may be acquired independently (e.g., in sequence), region 402 can be used to provide the user with a status update on the scan acquisition process. For example, each scan icon 1 to 5 in region 402 may be highlighted as its corresponding cube scan is being acquired, or is completed, as illustrated by highlighted scan icon 1. For instance, in one embodiment, the different scan icons 1 to 5 can be demarcated with a check-mark, or a highlighted border, or some other visual indicator as their corresponding cube scan is acquired and/or completed. In addition, if a user selects (or moves) any of scan icon 1 to 5 that indicates an already acquired scan, the system may respond by retaking that icon's corresponding cube scan for the montage. This may be the case, for example, if the operator is aware of some condition, such as an eye blink or movement of the patient that may lead to a reduced quality image. The cube scan's corresponding icon can be highlighted (e.g., by a blinking border or a differently colored border) to indicate that the cube scan is currently being re-acquired.

Figures 4B, 4C:
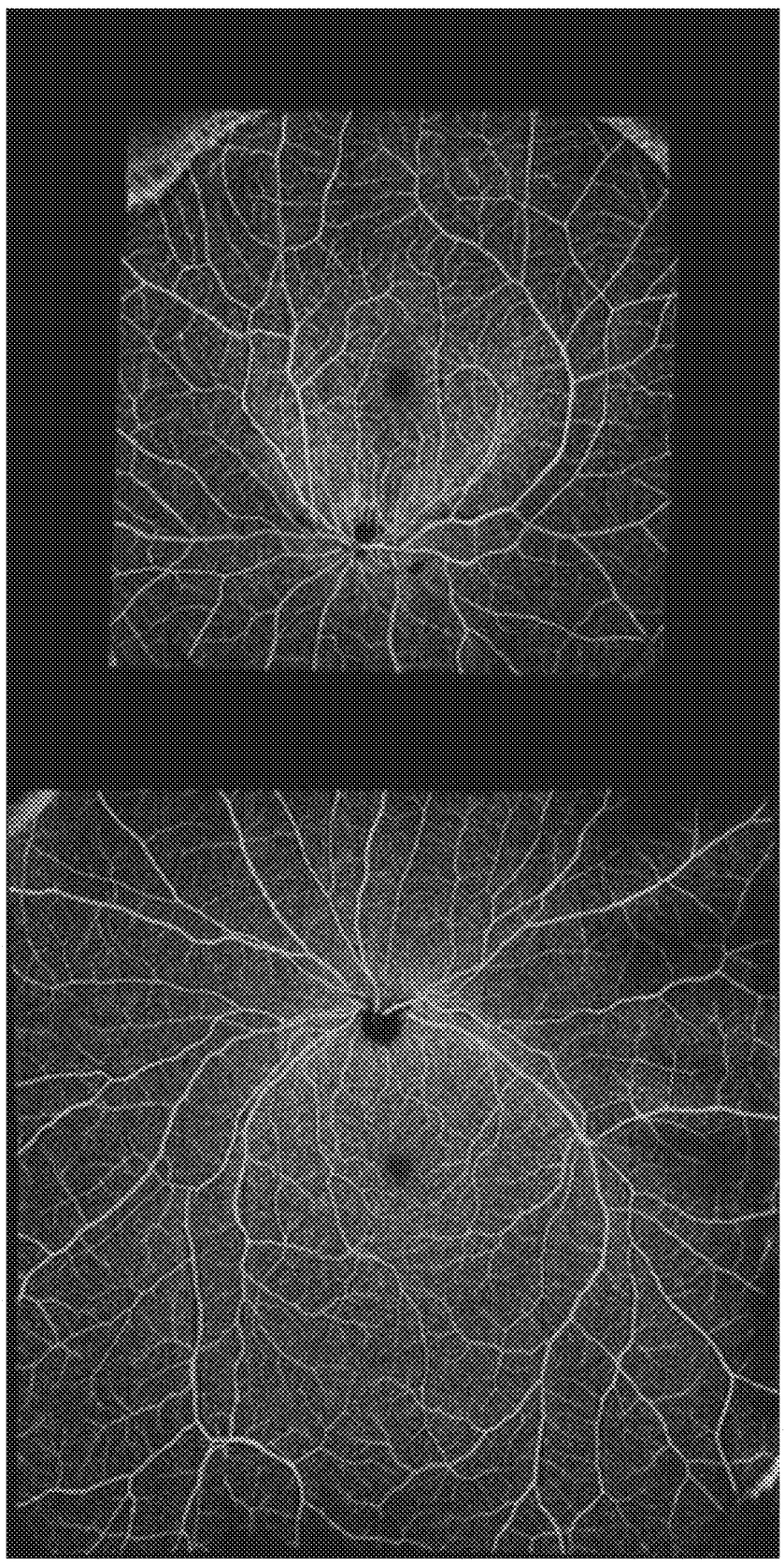
FIG. 4b and FIG. 4c illustrate montaged images that result from montaging constituent images with different amounts of overlap. The montage of FIG. 4b has a smaller overlap between its constituent images, as is suitable for an emmetropic eye, and provides a larger FOV. The montage of FIG. 4c has a larger overlap between its constituent images, as is suitable for a myopic eye, and provides a smaller FOV.

FIG. 4b and FIG. 4c illustrate montaged images that result from montaging constituent images with different amounts of overlap (such as indicated by scan options 401). FIG. 4b is a wide configuration (e.g., smaller overlap between sets of OCT scans) shown for an emmetropic eye. FIG. 4c is a narrow configuration (e.g., larger overlap between sets of OCT scans) shown for a myopic eye. The curvature of the eye can make it difficult to obtain OCT montages as it may lead to vignetting of B-scans, for example, because the variation of the optical path length of the scanning points across the retina may exceed the imaging depth of the system. This may be especially bad in the presence of myopia as illustrated on the right edge in FIG. 4c. To overcome this problem when acquiring multiple peripheral scans intended to be montaged, it is possible to adjust the location of the scans relative to the optical axis of the instrument.

As stated above, a user may choose to retake any scan used in a montaged image. The user may choose to retake an image before or after the montaged image is created. For example, the user interface may provide a preview screen on which each collected scan (as identified by scan icons 1 to 5) is displayed separately. At any time the user may select an already collected scan (e.g., either from this preview screen or from region 402) for rescanning. Optionally, the collected scans may not be montaged until after a user input indicating user approval is submitted. Further optionally, the collected images/scans may be montaged and the user may select (e.g., by means of any known user input device, such as a computer mouse, stylus, touch-sensitive screen, etc.) an individual scan within an already montaged image, and have the individually selected scan retaken. The montaged image may then be updated with the newly retaken scan.

Figure 4D:
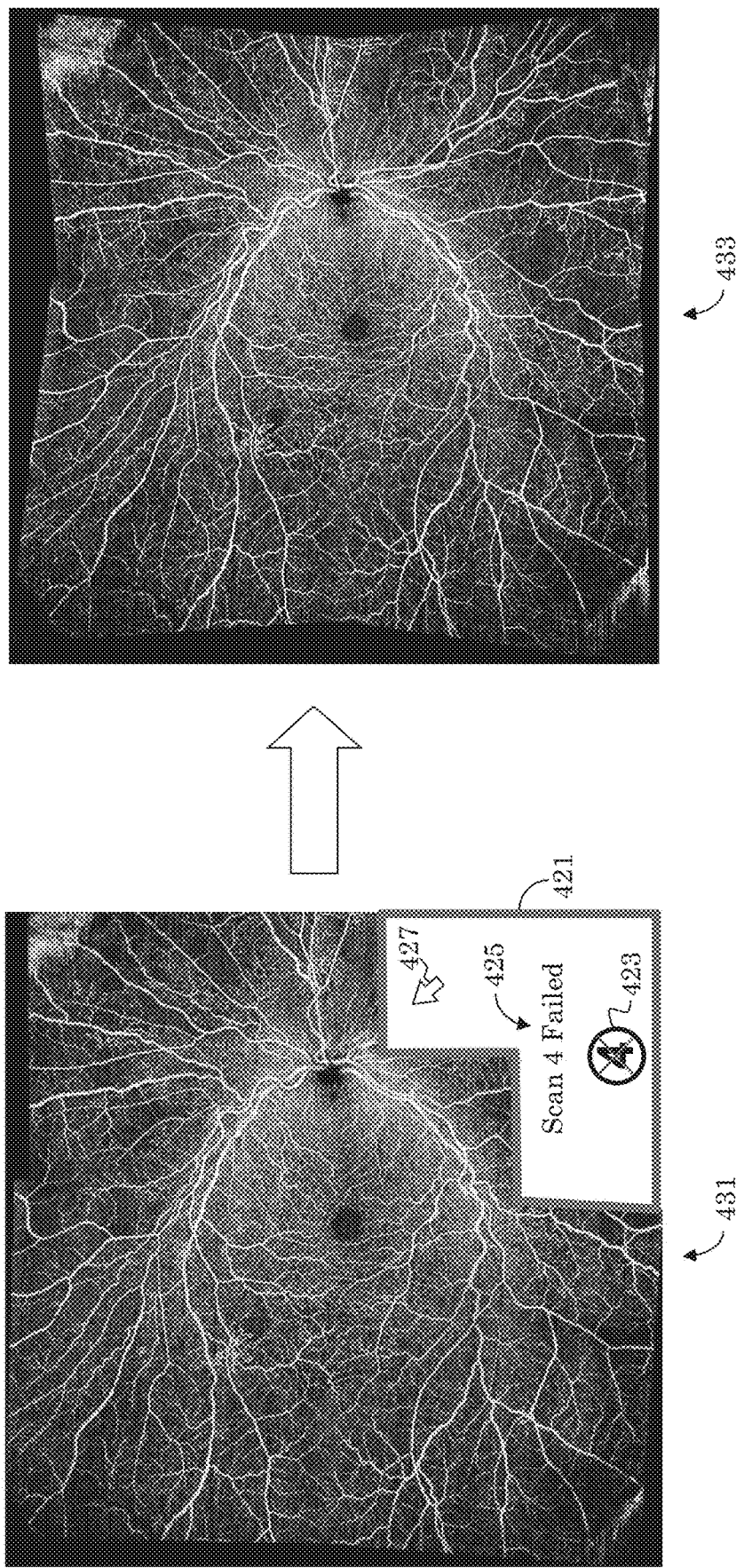
FIG. 4d illustrates a case where a montaged image is created using 4 successful scans out of a 5 scan option where one scan failed, and a case where the montage is recreated with all 5 successful scans.

Further alternatively, if a particular scan fails (such as if a scan from a selected scan option 401 fails), the montaged image may still be created using the scans that did not fail. FIG. 4d illustrates a case where a montaged image 431 is created using 4 successful scans of a 5 scan option where one scan failed, and a case where a montaged image 433 is recreated with all 5 successful scans. In the montaged image 431 with one or more missing, failed scans, a visual indicator may be provided in the montaged image 431 indicating which scan failed and is missing from the montaged image. This visual indicator may include a textual message 425 (e.g., a description of the type of failure and/or message identifying the failed scan), a graphic 423 (e.g., a graphic representation of failure and/or of a failed scan), and/or a highlighted border 421 indicating an outline of the failed scan within the montaged image. The visual indicator may further identify the scan number (e.g., scan icons 1 to 5) that failed and may be located at the relative location of where the failed scan would have been in the montaged image 431 if it had not failed. The user may then select this visual indicator in the montaged image by use of a user input device, such as pointer 427, and have the system retake the failed scan. The montaged image is then updated, as illustrated by montaged image 433 to include the retaken scan. Additionally, the user may adjust the relative location of the failed scan prior to retaking the failed scan. For example, the pointer 427 may be used to drag the location of outline 421 closer toward the center of montaged image 431 prior to rescanning the failed scan.

An example of a mechanism for adjusting the relative location of a scan is provided in FIGS. 5a to 5d. FIG. 5a illustrates an eye 501 having a stronger (e.g., higher) curvature of the retina at a Region A as compared to a Region B. Consequently, scan beams 502 adjusted for the retina surface in region B may not be well-suited for Region A, as illustrated by scan beams 503. While acquiring multiple cube scans, a cube scan placed in region A can be offset toward the central part of the retina (where the retina is flatter) to avoid vignetting, e.g., vignetting of the cube scan's B-scans.

FIG. 5b illustrates a scan configuration (including prescans) for a scan option consisting of five (cube) scans C1, P2, P3, P4, and P5 having predefined positions relative to each other, and which in the present example correspond to the five scan configuration of FIG. 4a. FIG. 5b shows an y-z view of an eye 501 on the left-hand side, and a scan configuration along the back (x-y view) of the eye 501b. The scan configuration of FIG. 5b includes one central (cube) scan C1 (shown in dark solid line) surrounded by four peripheral (cube) scans P2 to P5 (shown as dash lines or solid gray lines). Since the central scan C1 is located at an area of the retina having relatively low curvature, it may optionally be taken directly. The four periphery scans P2 to P5, however, span areas of the retina having higher curvatures. Therefore, a periphery scan may be preceded by a corresponding survey scan (or prescan) of the retinal area that is to be scanned by the periphery scan.

For illustration purposes, an example configuration of a survey scan as applied to periphery scan P4 (located at a position lower-right to central scan C1) is shown. It is to be understood that a similar survey scan may be applied to any cube scan in the scan configuration along the back of the eye 501b. A survey scan may consist of one or more survey B-scans to determine if the periphery scan should be offset, such as to obtain a larger FOV for the montaged image or to avoid errors such as vignetting. That is, the survey scans may be used to determine optimal positions for their corresponding cube scans or portions of cube scans, e.g., P2 to P5. A survey scan may be of lower resolution than its corresponding periphery scan, and its survey B-scan(s) may be located at or near the edges (e.g. along the margins) of the retinal area/region defined by the periphery scan that is to be collected. A survey scan may include one or more survey B-scans along a first dimension (e.g., the x-axis). For example, a survey scan may have a top horizontal survey B-scan SH1, a middle horizontal survey B-scan SH2, and a bottom horizontal B-scan SH3. Optionally, a survey scan may also include one or more vertical survey B-scans traversing the horizontal survey B-scans. The present example shows two vertical survey B-scans SV1 and SV2. The individual survey B-scans may then be examined to determine if their corresponding periphery scan should be offset.

For example, FIG. 5c shows survey B-scan SH1 of FIG. 5B, and illustrates how to determine if it is fully resolved. The depth coordinates of the A-scans of survey B-scan SH1 may be calculated to determine if individual A-scans are within the imaging depth range of the instrument. In FIG. 5c, all of the A-scans comprising survey B-scan SH1 are within the imaging depth range (along the z-axis) of the instrument, and so survey B-scan SH1 may be deemed to be fully resolved. Optionally, additional survey B-scans corresponding to periphery scan P4 (see FIG. 5b) may be examined to determine if they can be fully resolved. If all (or a select, representative sub-set of) the survey B-scans for a particular periphery scan are fully resolved, then it can be expected that the periphery scan corresponding to these survey B-cans would also be fully resolved, and no scan offset is necessary.

By contrast, FIG. 5d illustrates a case where it is determined that a cube scan should be offset, or shifted, due to part of at least one of its corresponding survey B-scan not being fully resolved within the imaging depth range of the instrument. FIG. 5d reproduces eye 501 of FIG. 5a and further demarcates on the eye the imaging depth of the instrument. For illustration purposes, imaging window 511 shows survey B-scan SH3, which corresponds to the bottom edge of the periphery scan P4 in FIG. 5b. Survey B-scan SH3 is shown to not be fully resolved within the imaging depth range of the instrument, e.g., its right-most portion 513 is cut-off. That is, the A-scans that correspond to portion 513 are outside the imaging depth range, which may cause vignetting. The A-scans in region 513 may also introduce mirror artifacts 515, such as due to the complex conjugate effect of the Fourier transforms used to resolve A-scans.

To avoid vignetting and other artifacts, the application can calculate, from the number of A-scans that are not resolved within the imaging window 511, a scan offset to shift a corresponding cube scan closer to the macula (and/or the central scan) corresponding to a "flatter" region of the retina. For example, portion 513 may identify a scan offset (e.g., along the x-axis) to permit the survey B-scan SH3 to be fully resolved. This scan offset may then be applied to the corresponding periphery scan P4, as a whole, or individually to the corresponding B-scan(s) within periphery scan P4, to avoid artifacts in the montaged image. For example, imaging window 517 shows a B-scan of the periphery scan P4 that has been offset by an amount determined from portion 513. Consequently, all A-scans within this B-scan are fully resolved and vignetting is avoided.

However, if the survey B-scans are not vignetted, such as survey B-scan SH1 in FIG. 5c, the application may optionally determine a scan offset to shift the corresponding cube scan further to the periphery of the retina (e.g. reduce its overlap with the central scan without introducing vignetting) corresponding to a "steeper" region of the retina to get the largest field of view possible for the final montaged image. This offset may be determined by extrapolating the survey B-scan SH1 beyond its imaging window, or by repeatedly shifting and retaking the survey B-scan SH1 (while maintaining an overlap with the area of central scan C1) until vignetting is encountered. Alternatively, the known refractive error or axial length of the eye could be used to predict the best montage scan pattern for a particular eye.

Optionally, the above-described use of survey scans (e.g., prescans) to determine preferred, or optimal, scan regions for periphery cube scans may be used to automatically select, or suggest, one of the scan options 401 (see FIG. 4a) whose configuration is close (or closest) to the determined preferred scan regions. It is to be further understood that the above-described use of survey scans may also be used to modify any selected scan option 401 to move (or recommend the moving of) any of its individual, constituent scans to positions more closely aligned with their preferred scan regions as determined from their corresponding survey scans. Thus, the location of any individual scan (e.g., as identified by scan icons 1 to 5 in FIG. 4a), may be individually adjusted/altered after selection of a specific scan option 401 by mean of a user input device or automatically in accordance with its correspondingly determined optimal scan region.

In another aspect of the present application, the size (e.g. area) of the cube scans collected for a montage can be varied. Larger size (e.g., larger field of view) cube scans could be used centrally where the retina is flatter and smaller field of view cube scans could surround this central cube scan over areas where the retinal curvature prevents larger field of view cube scans. It may also be helpful to change the resolution of individual cube scans in either the transverse or axial directions. For instance, near the fovea, it is desirable to have densely sampled scans, but in the periphery, it may be sufficient to sample less densely. Alternately, it may be useful to have deeper scans with lower axial resolution for more steeply curved eyes, such as those with myopia.

Some retinal tissue may appear flat over a large region. FIG. 6a is an example showing a case where a wider field of view volume scan can collect all of the data over a flat area of retinal tissue with good resolution. Other retinal tissue may have substantially more curvature. FIG. 6b illustrates a case that requires a larger number of volumes with smaller transverse field of views to fully capture the retinal tissue with high resolution due to the retinal tissue having substantially more curvature. FIG. 6c shows, in two dimensions, the montaging of multiple retina samplings (scans) with different heights and widths of scan. Individual retinal samplings are indicated by highlighted rectangular regions. The same principle would apply in three dimensions.

Flow Projection Correction

OCT Angiography images are susceptible to flow projection artifacts and many different techniques for removing these projection artifacts have been proposed (see for example, "Projection-resolved optical coherence tomographic angiography", by Miao Zhang et al., Biomed Opt Express. 2016 Mar. 1; 7(3): 816-828; and "Minimizing projection artifacts for accurate presentation of choroidal neovascularization in OCT micro-angiography", by Anqi Zhang et al., Biomed Opt Express. 2015 Oct. 1; 6(10): 4130-4143). In some cases, it is desirable for an OCT imaging system to allow the user to select whether or not to apply such a correction to the imaging data for instance through the use of a user selectable icon or button on the user interface of the system or external processing. When the user enables the flow projection removal, the processor could function to apply the projection artifact removal algorithm first to the deeper slabs of all of the constituent en face images. The projection-artifact-free constituent images are then montaged as described above. The user can also not select this artifact removal function and in this case the en face images are not corrected for flow projection. FIG. 6d shows a montaged image where flow projection artifact removal has not been enabled, in this case via selection of a selectable button 609, while FIG. 6e shows a case where the feature was enabled by means of the selectable button 609. The removal, or lack of removal, of artifacts in images may be displayed/visualized using a depth-encoded, color coding scheme. For example, projection artifacts in a deeper slab may be displayed/identified using the a blue color. Consequently, the montaged image of FIG. 6e, which has projection artifacts removed, may appear "redder" than when the projection artifacts are not removed due to the blue color component of the projection artifacts in the deeper slab having been removed.

Distortion correction of wide field OCT images prior to montaging

The scan angle at the pupil plane is not a linear function of the scanning element in the ophthalmic system, typically a galvanometer. This can lead to optical distortion in the image (a change of magnification off the field). The OCT image can be corrected for distortion by encoding the x and y galvo positions such as to compensate for the known distortion of the optical system—This correction can be done while acquiring the scan rather than by post-processing of the en face image. The A-scans are no longer evenly distributed along the B-scans but have varying spacing over the length of the B-scans. This solution avoids an extra step in post-processing.

Montage Location Check

FIG. 7a illustrates a workflow for checking the locations of individual, constituent scans within a montage. Once montaging of the images is complete, it may be desirable to check the location of the individual scans in the montage. In an aspect of this invention shown in FIG. 7a, the constituent images are received from the acquisition workflow (701). The images are montaged (702) and the locations of the constituent images within the montaged image are identified (703) for example by identifying a pixel number from each image and locating that pixel in the composite image as illustrated in FIG. 7b where an "x" indicate specific pixel locations. These locations can then be compared (704) with the relationships between the pre-defined scan locations (705). For example, if it is known that the "x" corresponding to image 1 should be above the "x" of image 4, to the right of the "x" of image 0 and to the left of the "x" of image 3, as is shown in FIG. 7b, then it can be inferred that image 1 is in its correct, designated position relative to image 4, image 0 and image 3. But if the "x" of image 1 were not in its expected position relative to the other constituent images, then it could be inferred that image 1 is not in its designated (expected) position, and an error notification could be issued. This can be used to detect misplacement of any constituent image within the final montaged image (FIG. 7c) and to inform the instrument operator (706) if a misplacement is detected. The user could then review the montaged image and determine if there is in fact a misplaced constituent image, and if so, retake the one or more misplaced images.

Example Computer System

Unless otherwise indicated, the processing units 121 and 212 that have been discussed herein (e.g., in reference to FIGS. 1 and 2) may be implemented with a computer system configured to perform the functions that have been described herein for this unit. For instance, the processing unit 221 can be implemented with the computer system 1000, as shown in FIG. 8. The computer system 1000 may include one or more processors 1002, one or more memories 1004, a communication unit 1008, an optional display 1010, one or more input devices 1012, and a data store 1014. The display 1010 is shown with dotted lines to indicate it is an optional component, which, in some instances, may not be a part of the computer system 1000. In some embodiments, the display 1010 is the display 122 or 213 that has been discussed herein in reference to FIGS. 1 and 2.

The components 1002, 1004, 1008, 1010, 1012, and 1014 are communicatively coupled via a communication or system bus 1016. The bus 1016 can include a conventional communication bus for transferring data between components of a computing device or between computing devices. It should be understood that the computing system 1000 described herein is not limited to these components and may include various operating systems, sensors, video processing components, input/output ports, user interface devices (e.g., keyboards, pointing devices, displays, microphones, sound reproduction systems, and/or touch screens), additional processors, and other physical configurations.

The processor(s) 1002 may execute various hardware and/or software logic, such as software instructions, by performing various input/output, logical, and/or mathematical operations. The processor(s) 1002 may have various computing architectures to process data signals including, for example, a complex instruction set computer (CISC) architecture, a reduced instruction set computer (RISC) architecture, and/or architecture implementing a combination of instruction sets. The processor(s) 1002 may be physical and/or virtual, and may include a single core or plurality of processing units and/or cores. In some embodiments, the processor(s) 1002 may be capable of generating and providing electronic display signals to a display device, such as the display 1010, supporting the display of images, capturing and transmitting images, performing complex tasks including various types of feature extraction and sampling, etc. In some embodiments, the processor(s) 1002 may be coupled to the memory(ies) 1004 via a data/communication bus to access data and instructions therefrom and store data therein. The bus 616 may couple the processor(s) 1002 to the other components of the computer system 1000, for example, the memory(ies) 1004, the communication unit 1008, or the data store 1014.

The memory(ies) 1004 may store instructions and/or data that may be executed by the processor(s) 1002. In some embodiments, the memory(ies) 1004 may also be capable of storing other instructions and data including, for example, an operating system, hardware drivers, other software applications, databases, etc. The memory(ies) 1004 are coupled to the bus 1016 for communication with the processor(s) 602 and other components of the computer system 1000. The memory(ies) 1004 may include a non-transitory computer-usable (e.g., readable, writeable, etc.) medium, which can be any apparatus or device that can contain, store, communicate, propagate or transport instructions, data, computer programs, software, code, routines, etc. for processing by or in connection with the processor(s) 1002. A non-transitory computer-usable storage medium may include any and/or all computer-usable storage media. In some embodiments, the memory(ies) 1004 may include volatile memory, non-volatile memory, or both. For example, the memory(ies) 1004 may include a dynamic random access memory (DRAM) device, a static random access memory (SRAM) device, flash memory, a hard disk drive, a floppy disk drive, a CD ROM device, a DVD ROM device, a DVD RAM device, a DVD RW device, a flash memory device, or any other mass storage device known for storing instructions on a more permanent basis.

The computer system for the processing unit 121 or 212 may include one or more computers or processing units at the same or different locations. When at different locations, the computers may be configured to communicate with one another through a wired and/or wireless network communication system, such as the communication unit 1008. The communication unit 1008 may include network interface devices (I/F) for wired and wireless connectivity. For example, the communication unit 1008 may include a CAT-type interface, USB interface, or SD interface, transceivers for sending and receiving signals using Wi-Fi™; Bluetooth®, or cellular communications for wireless communication, etc. The communication unit 1008 can link the processor(s) 1002 to a computer network that may in turn be coupled to other processing systems.

The display 1010 represents any device equipped to display electronic images and data as described herein. The display 1010 may be any of a conventional display device, monitor or screen, such as an organic light-emitting diode (OLED) display, a liquid crystal display (LCD). In some embodiments, the display 1010 is a touch-screen display capable of receiving input from one or more fingers of a user. For example, the device 1010 may be a capacitive touch-screen display capable of detecting and interpreting multiple points of contact with the display surface.

The input device(s) 1012 are any devices for inputting data on the computer system 1000. In some embodiments, an input device is a touch-screen display capable of receiving input from one or more fingers of the user. The functionality of the input device(s) 1012 and the display 1010 may be integrated, and a user of the computer system 1000 may interact with the system by contacting a surface of the display 1010 using one or more fingers. In other embodiments, an input device is a separate peripheral device or combination of devices. For example, the input device(s) 1012 may include a keyboard (e.g., a QWERTY keyboard) and a pointing device (e.g., a mouse or touchpad). The input device(s) 1012 may also include a microphone, a web camera, or other similar audio or video capture devices.

The data store 1014 can be an information source capable of storing and providing access to data. In the depicted embodiment, the data store 1014 is coupled for communication with the components 1002, 1004, 1008, 1010, and 1012 of the computer system 1000 via the bus 1016.

In the above description, for purposes of explanation, numerous specific details are set forth in order to provide a thorough understanding of the specification. It should be apparent, however, that the subject matter of the present application can be practiced without these specific details. It should be understood that the reference in the specification to "one embodiment", "some embodiments", or "an embodiment" means that a particular feature, structure, or characteristic described in connection with the embodiment is included in one or more embodiments of the description. The appearances of the phrase "in one embodiment" or "in some embodiments" in various places in the specification are not necessarily all referring to the same embodiment(s).

Furthermore, the description can take the form of a computer program product accessible from a computer-usable or computer-readable medium providing program code for use by or in connection with a computer or any instruction execution system. For the purposes of this description, a computer-usable or computer readable medium can be any apparatus that can contain, store, communicate, propagate, or transport the program for use by or in connection with the instruction execution system, apparatus, or device. The foregoing description of the embodiments of the present subject matter has been presented for the purposes of illustration and description. It is not intended to be exhaustive or to limit the present embodiment of subject matter to the precise form disclosed. Many modifications and variations are possible in light of the above teaching. It is intended that the scope of the present embodiment of subject matter be limited not by this detailed description, but rather by the claims of this application. As will be understood by those familiar with the art, the present subject matter may be embodied in other specific forms without departing from the spirit or essential characteristics thereof. Furthermore, it should be understood that the modules, routines, features, attributes, methodologies and other aspects of the present subject matter can be implemented using hardware, firmware, software, or any combination of the three.

We claim:

1. A method for collecting a set of images for montaging using an ophthalmic imaging system, said method comprising:
   providing a scan option via a user interface, wherein the scan option comprises two or more scans covering different transverse regions on the retina of a patient, said regions containing some overlapping portion;
   upon selection of the scan option, initiating capture of the two or more scans for the selected scan option; and
   displaying the collected two or more scans on a display for approval;
   in response to user selection of any of the displayed scans by use of a user input device, automatically recapturing the selected scans and updating the display with the recaptured scans.

2. The method of claim 1, wherein the two or more scans displayed for approval are not montaged, and the displayed scans are montaged after a user input indicating user approval.

3. The method of claim 1, wherein the two or more scans displayed for approval are displayed as a montaged image, and said user selection is applied to at least one constituent scan within the montaged image.

4. The method as recited in claim 3, wherein the two or more scans have preassigned displacement positions relative to each other within the montaged image, the method further comprising:
   processing the montaged image using a processor to determine if the two or more scans are in their preassigned displacement positions relative to each other in the montaged image; and
   identifying any misplaced scan or displaying an error indicator based on the determination.

5. The method as recited in claim 3, wherein the two or more scans have preassigned displacement positions relative to each other within the montaged image, the method further comprising:
   providing a scan displacement input in the user interface, wherein the preassigned displacement positions relative to each other of the two or more scans is adjustable by use of the scan displacement input.

6. The method of claim 3, further comprising:
   in response to failing to capture any of the two or more scans for the selected scan option, excluding the failed scans from the montaged image, and displaying a failure indicator within the montaged image for each failed scan at a location within the montaged image corresponding to where failed scans would have been if it had not failed.

7. The method of claim 6, further comprising:
in response to user selection of any displayed failure indicator, automatically recapturing the scans corresponding to the selected failure indictors and updating the montaged image with the recaptured scan.

8. The method of claim 7, wherein the failure indicators include at least one of a textual description of failure, a graphic representation of failure, and a highlighted border indicating an outline of the failed scan within the montaged image.

9. The method as recited in claim 1, wherein the ophthalmic imaging system is one of a fundus imaging system and an optical coherence tomography system.

10. The method as recited in claim 1, wherein the two or more scans cover different sized regions of the retina.

11. The method as recited in claim 1, wherein the two or more scans have different scan resolutions.

12. The method as recited in claim 1, further comprising:
assigning a quality measure to each of the captured two or more scans;
wherein captured scans having higher quality measures comprise larger fractions of the montaged image.

13. The method as recited in claim 1, wherein the user interface further includes a user input for removing artifacts.

14. A method for generating a montaged fundus image of an eye using an ophthalmic imaging system, said method comprising:
providing a plurality of scan options via a user interface, wherein each scan option contains two or more scans covering different transverse regions on the retina of a patient, said regions containing some overlapping portion, wherein the scan options differ in the amount of overlap between their respectively contained two or more scans;
upon selection of a scan option within the plurality of scan options, initiating capture of the two or more scans of the selected scan option;
combining the two or more captured scans into a single montaged image; and
storing or displaying the montaged image or a further analysis thereof.

15. The method as recited in claim 14, wherein the user interface further provides a separate scan status for each of two or more scans during the capture of the two or more scans.

16. The method as recited in claim 15, wherein the user interface further provides a user input for recapturing a selected one or more of the two or more scans during the capture of the two or more scans.

17. The method as recited in claim 14, wherein the ophthalmic imaging system is an optical coherence tomographic system and each of the plurality of scan options is separately optimized for a different eye curvature.

18. The method as recited in claim 14, further comprising performing a prescan of the eye to determine an optimal scan pattern for use during the capture of the two or more scans based on the curvature of the eye.

19. The method as recited in claim 18, wherein the prescan is of lower resolution than the capture of the two or more scans, and one of the plurality of scan options is selected based on the determined optimal scan pattern.

20. The method as recited in claim 14, wherein the ophthalmic imaging system is an optical coherence tomographic (OCT) system, and the two or more scans of one of the plurality of scan options includes a central scan and a periphery scan that is peripheral to the central scan, the method further comprising:
prior to the capture of the periphery scan, collecting a survey scan within a region corresponding to where the periphery scan is to be captured;
in response to a portion of the survey scan not being fully resolved within the imaging depth capability of the OCT system, shifting the region corresponding to where the periphery scan is to be captured to increase its overlap with the central scan.

21. The method as recited in claim 14, wherein the ophthalmic imaging system is an optical coherence tomographic (OCT) system, and the two or more scans of one of the plurality of scan options includes a central scan and a periphery scan that is peripheral to the central scan, the method further comprising:
prior to the capture of the periphery scan, collecting a survey scan within a region corresponding to where the periphery scan is to be captured;
in response to the survey scan being fully resolved within the imaging depth capability of the OCT system, doing one of the following:
collecting the periphery scan within the region where the survey scan was collected; or
shifting the region corresponding to where the periphery scan is to be captured to decrease its overlap with the central scan.

22. The method as recited in claim 14, wherein the user interface further includes a user input for removing artifacts from the two or more captured scans.

23. The method as recited in claim 14, wherein the two or more scans have preassigned displacement positions relative to each other, the method further comprising:
processing the montaged image using a processor to determine if the two or more scans are in their preassigned displacement positions relative to each other in the montaged image; and
identifying any misplaced scan or displaying an error indicator based on the determination.

24. The method as recited in claim 14, further comprising:
assigning a quality measure to each of the captured two or more scans;
wherein captured scans having higher quality measures comprise larger fractions of the montaged image.

* * * * *

UNITED STATES PATENT AND TRADEMARK OFFICE
CERTIFICATE OF CORRECTION

PATENT NO. : 11,000,187 B2
APPLICATION NO. : 16/123079
DATED : May 11, 2021
INVENTOR(S) : Sophie Kubach et al.

Page 1 of 1

It is certified that error appears in the above-identified patent and that said Letters Patent is hereby corrected as shown below:

On the Title Page

On the page 2, in Column 2, under "Other Publications", Line 12, delete "Reflectomety"," and insert -- Reflectometry", --, therefor.

In the Specification

In Column 19, Line 10, before "a" delete "the".

Signed and Sealed this
Seventeenth Day of August, 2021

Drew Hirshfeld
*Performing the Functions and Duties of the*
*Under Secretary of Commerce for Intellectual Property and*
*Director of the United States Patent and Trademark Office*